United States Patent
Pan et al.

(10) Patent No.: US 11,801,252 B2
(45) Date of Patent: Oct. 31, 2023

(54) PHARMACEUTICAL COMPOSITION

(71) Applicant: Jiangsu Hengrui Medicine Co., Ltd., Jiangsu (CN)

(72) Inventors: Caiyun Pan, Jiangsu (CN); Ailing Chen, Jiangsu (CN); Kai Pan, Jiangsu (CN); Kai Liu, Jiangsu (CN); Zhirong Mo, Jiangsu (CN)

(73) Assignee: Jiangsu Hengrui Pharmaceuticals Co., Ltd., Jiangsu (CN)

( * ) Notice: Subject to any disclaimer, the term of this patent is extended or adjusted under 35 U.S.C. 154(b) by 0 days.

(21) Appl. No.: 17/653,587

(22) Filed: Mar. 4, 2022

(65) Prior Publication Data
US 2022/0280536 A1    Sep. 8, 2022

Related U.S. Application Data

(60) Provisional application No. 63/200,435, filed on Mar. 5, 2021.

(51) Int. Cl.
  A61K 31/58    (2006.01)
  A61K 9/20     (2006.01)
  A61K 9/16     (2006.01)
  A61K 9/00     (2006.01)

(52) U.S. Cl.
  CPC ............ *A61K 31/58* (2013.01); *A61K 9/0053* (2013.01); *A61K 9/1694* (2013.01); *A61K 9/2013* (2013.01); *A61K 9/2018* (2013.01); *A61K 9/2027* (2013.01); *A61K 9/2054* (2013.01)

(58) Field of Classification Search
  CPC .... A61K 31/58; A61K 9/0053; A61K 9/1694; A61K 9/2013; A61K 9/2018; A61K 9/2027; A61K 9/2054
  USPC ........................................................ 514/176
  See application file for complete search history.

(56) References Cited

U.S. PATENT DOCUMENTS

2014/0287039 A1*  9/2014  Bosch .................. A61K 31/573
                                                         540/95

* cited by examiner

*Primary Examiner* — Kristin A Vajda
(74) *Attorney, Agent, or Firm* — Ice Miller LLP

(57) ABSTRACT

The present disclosure relates to a pharmaceutical composition. Specifically, a pharmaceutical composition of abiraterone acetate is provided, wherein a 300 mg dose of abiraterone acetate is bioequivalent to a 1000 mg dose of Zytiga® in healthy male subjects in a fasting state.

21 Claims, No Drawings

PHARMACEUTICAL COMPOSITION

CROSS-REFERENCE TO RELATED APPLICATION

This application is a non-provisional application claiming priority to U.S. Patent Application No. 63/200,435 filed Mar. 5, 2021, the disclosure of which is incorporated herein by reference in its entirety.

FIELD OF THE INVENTION

The present invention belongs to the field of pharmaceutical preparations, and specifically relates to a pharmaceutical composition of abiraterone acetate.

BACKGROUND OF THE INVENTION

Abiraterone is a CYP17 inhibitor for inhibiting the biosynthesis of androgen and estrogen. The acetate of this compound is approved in the United States for the treatment of castration-resistant prostate cancer. The prescribing information of Zytiga® tablets recommends a daily oral 1000 mg in combination with oral prednisone (5 mg) for the treatment of metastatic castration-resistant prostate cancer. At the same time, it is recommended to use it on an empty stomach, and no food should be consumed for at least 2 hours before the dose is taken and for at least 1 hour after the dose is taken. Food has a great impact on the oral bioavailability of abiraterone. $C_{max}$ and $AUC_{0-\infty}$ of abiraterone are approximately 17- and 10-fold higher, respectively, compared to administration in the fasting state. At the same time, in terms of clinical efficacy, Zytiga®, a commercially available product, exhibits poor bioavailability and large inter-individual differences. Therefore, researchers in pharmaceutical preparations field urgently need new pharmaceutical preparations. For example, WO2014145813 includes the development of a nano preparation of abiraterone acetate, which can achieve bioequivalence between a 500 mg dose of a unit dose form and a 1000 mg dose of Zytiga® tablets in healthy male subjects in a fasting state. However, the individual differences and food effects are still not effectively resolved.

There are two main ways to improve the oral bioavailability of drugs. One way is to change the physical and chemical properties of drugs to improve their membrane permeability or to improve their dissolution characteristics, such as micronization technology, solid dispersion technology, inclusion technology, etc. For example, CN103813794A discloses that 17-(3-pyridyl)androsta-5,16-diene-3β-acetate analog is dispersed in a water-soluble polymer carrier material to prepare a solid dispersion to solve the dissolution problem of the drug. CN103070828B discloses using povidone as a carrier material to prepare a solid dispersion to solve the similar problem. The other way is to improve the characteristics of the membrane to increase the membrane permeability of the drug, or to inhibit the efflux pump to prevent the body from efflux of the absorbed drug, that is, the use of oral absorption enhancers. For example, CN102123697A discloses the addition of an absorption enhancer of sodium N-(8-(2-hydroxybenzoyl)amino)caprylate (SNAC) or sodium N-(8-(2-hydroxybenzoyl)amino)decanoate (SNAD), or a combination thereof to enhance the absorption of proteins and protease inhibitors through the intestinal mucosal barrier to solve the problem of bioavailability of GLP-1 analogs in the composition.

In addition, the use of absorption enhancers to improve the individual differences of a drug in different patients has not been reported in the literature.

SUMMARY OF THE INVENTION

The present disclosure provides a pharmaceutical composition wherein a 300 mg dose of abiraterone acetate is bioequivalent to a 1000 mg dose of Zytiga® in healthy male subjects in a fasting state. In some embodiments, a mean blood plasma $C_{max}$ of 209±142 ng/ml is provided upon orally administering 300 mg dose of abiraterone acetate to a group of healthy male subjects in a fasting state.

In some embodiments, a median $T_{max}$ of 1 hour is provided upon orally administering 300 mg dose of abiraterone acetate to a group of healthy male subjects in a fasting state.

In some embodiments, a mean blood plasma $AUC_{0-t}$ of 620.08±370.19 ng·h/ml is provided upon orally administering 300 mg dose of abiraterone acetate to a group of healthy male subjects in a fasting state.

In some embodiments, a mean blood plasma $AUC_{0-\infty}$ of 627.60±370.44 ng·h/ml is provided upon orally administering 300 mg dose of abiraterone acetate to a group of healthy male subjects in a fasting state.

In another aspect, a 80 to 125% of the mean blood plasma $C_{max}$ of 209 ng/ml is provided upon orally administering 300 mg dose of abiraterone acetate to a group of healthy male subjects in a fasting state.

In some embodiments, a 80 to 125% of the mean blood plasma $AUC_{0-t}$ of 620.08 ng·h/ml is provided upon orally administering 300 mg dose of abiraterone acetate to a group of healthy male subjects in a fasting state.

In some embodiments, a 80 to 125% of the mean blood plasma $AUC_{0-\infty}$ of 627.60 ng·h/ml is provided upon orally administering 300 mg dose of abiraterone acetate to a group of healthy male subjects in a fasting state.

In addition, compared to ZYTIGA® and YONSA®, food has less influence on the pharmaceutical composition of the present disclosure. In some embodiments, the mean blood plasma $C_{max}$ is up to 3 times that of the fasting state, and may be 3 times, 2.8 times, 2.6 times, 2.4 times, 2.2 times, 2.0 times 1.8 times, 1.6 times, 1.4 times, 1.2 times, 1.0 times or less or any value between the two values that of the fasting state, upon orally administering 300 mg dose of abiraterone acetate to a group of healthy male subjects in the high-fat state (total calories about 800 to 1000 kcal, of which about 50% of the calories come from fat).

In other embodiments, the mean blood plasma $AUC_{0-t}$ is up to 3 times that of the fasting state, and may be 3.0 times, 2.8 times, 2.6 times, 2.4 times, 2.2 times, 2.0 times, 1.8 times, 1.6 times, 1.4 times, 1.2 times, 1.0 times or less or any value between the two values that of the fasting state, upon orally administering 300 mg dose of abiraterone acetate to a group of healthy male subjects in the high-fat state (total calories about 800 to 1000 kcal, of which about 50% of the calories come from fat).

In other embodiments, the mean blood plasma $AUC_{0-\infty}$ is up to 3 times that of the fasting state, and may be 3.0 times, 2.8 times, 2.6 times, 2.4 times, 2.2 times, 2.0 times, 1.8 times, 1.6 times, 1.4 times, 1.2 times, 1.0 times or less or any value between the two values that of the fasting state, upon orally administering 300 mg dose of abiraterone acetate to a group of healthy male subjects in the high-fat state (total calories about 800 to 1000 kcal, of which about 50% of the calories come from fat).

In some embodiments, the intra-individual coefficient of variation (CV) of the mean blood plasma $AUC_{0-t}$ of abiraterone is less than 25% or less, and may be 25.0%, 24.5%, 24.0%, 23.5%, 23.0%, 22.5%, 22.0%, 21.5%, 21.0%, 20.5%, 20.0%, 19.5%, 19.0%, 18.5%, 18.0%, 17.5%, 17.0%, 16.5%, 16.0%, 15.5%, 15.0%, 14.5%, 14.0%, 13.5%, 13.0%, 12.5%, 12.0%, 11.5%, 11.0%, 10.5%, 10.0% or less or any value between the two values, upon orally administering 300 mg dose of abiraterone acetate to a group of healthy male subjects in a fasting state. In some embodiments, the intra-individual coefficient of variation (CV) of the mean blood plasma $AUC_{0-\infty}$ of abiraterone is about 15%, upon orally administering 300 mg dose of abiraterone acetate to a group of healthy male subjects in a fasting state.

In some embodiments, the intra-individual coefficient of variation (CV) of the mean blood plasma $AUC_{0-t}$ of abiraterone is less than 25% or less, and may be 25.0%, 24.5%, 24.0%, 23.5%, 23.0%, 22.5%, 22.0%, 21.5%, 21.0%, 20.5%, 20.0%, 19.5%, 19.0%, 18.5%, 18.0%, 17.5%, 17.0%, 16.5%, 16.0%, 15.5%, 15.0%, 14.5%, 14.0%, 13.5%, 13.0%, 12.5%, 12.0%, 11.5%, 11.0%, 10.5%, 10.0% or less or any value between the two values, upon orally administering 300 mg dose of abiraterone acetate to a group of healthy male subjects in a fasting state. In some embodiments, the intra-individual coefficient of variation (CV) of the mean blood plasma $AUC_{0-t}$ of abiraterone is about 15%, upon orally administering 300 mg dose of abiraterone acetate to a group of healthy male subjects in a fasting state.

In another aspect, in some embodiments, the intra-individual coefficient of variation (CV) of the mean blood plasma $AUC_{0-t}$ is reduced by at least 5% or more, and may be reduced by 5.0%, 5.2%, 5.4%, 5.6%, 5.8%, 6.0%, 6.2%, 6.4%, 6.6%, 6.8%, 7.0%, 7.2%, 7.4%, 7.6%, 7.8%, 8.0%, 8.2%, 8.4%, 8.6%, 8.8%, 9.0%, 9.2%, 9.4%, 9.6%, 9.8%, 10.0%, 10.2%, 10.4%, 10.6%, 10.8%, 11.0%, 11.2%, 11.4%, 11.6%, 11.8%, 12.0%, 12.2%, 12.4%, 12.6%, 12.8%, 13.0%, 13.2%, 13.4%, 13.6%, 13.8%, 14.0%, 14.2%, 14.4%, 14.6%, 14.8%, 15.0% or more or any value between the two values, compared to the 1000 mg dose of Zytiga®, upon orally administering 300 mg dose of abiraterone acetate to a group of healthy male subjects in a fasting state. In some embodiments, the intra-individual coefficient of variation (CV) of the mean blood plasma $AUC_{0-t}$ is reduced by 10% compared to the 1000 mg dose of Zytiga®, upon orally administering 300 mg dose of the abiraterone acetate pharmaceutical composition.

In other embodiments, the intra-individual coefficient of variation (CV) of the mean blood plasma $AUC_{0-\infty}$ is reduced by at least 5% or more, and may be reduced by 5.0%, 5.2%, 5.4%, 5.6%, 5.8%, 6.0%, 6.2%, 6.4%, 6.6%, 6.8%, 7.0%, 7.2%, 7.4%, 7.6%, 7.8%, 8.0%, 8.2%, 8.4%, 8.6%, 8.8%, 9.0%, 9.2%, 9.4%, 9.6%, 9.8%, 10.0%, 10.2%, 10.4%, 10.6%, 10.8%, 11.0%, 11.2%, 11.4%, 11.6%, 11.8%, 12.0%, 12.2%, 12.4%, 12.6%, 12.8%, 13.0%, 13.2%, 13.4%, 13.6%, 13.8%, 14.0%, 14.2%, 14.4%, 14.6%, 14.8%, 15.0% or more or any value between the two values, compared to the 1000 mg dose of Zytiga®, upon orally administering 300 mg dose of abiraterone acetate to a group of healthy male subjects in a fasting state. In other embodiments, the intra-individual coefficient of variation (CV) of the mean blood plasma $AUC_{0-\infty}$ is reduced by 11% compared to the 1000 mg dose of Zytiga®, upon orally administering 300 mg dose of the abiraterone acetate pharmaceutical composition.

In other embodiments, the pharmaceutical composition of the present disclosure comprises 150 mg of abiraterone acetate.

In other embodiments, the pharmaceutical composition of the present disclosure is an unit dosage composition. Some embodiments provide an unit dosage pharmaceutical composition with a tablet weight of about 636 mg.

In another aspect, the pharmaceutical composition of the present disclosure comprises abiraterone acetate and an absorption enhancer.

In some embodiments, the absorption enhancer in the pharmaceutical composition is at least one selected from the group consisting of capric acid, sodium caprate, potassium caprate, N-(10-[2-hydroxybenzoyl]amino)capric acid, caprylic acid, sodium caprylate, potassium caprylate, N-(5-chlorosalicyloyl)-8-aminocaprylic acid, 8-(salicylamido)caprylic acid and sodium 8-(salicylamido)caprylate. In some embodiments, the absorption enhancer in the pharmaceutical composition is at least one of 8-(salicylamido)caprylic acid and sodium 8-(salicylamido)caprylate. In some embodiments, the absorption enhancer in the pharmaceutical composition is sodium 8-(salicylamido)caprylate.

Further, in some embodiments, the weight ratio of the absorption enhancer to abiraterone acetate in the pharmaceutical composition is 1:100 to 100:1, and may be 1:100, 1:99, 1:98, 1:97, 1:96, 1:95, 1:94, 1:93, 1:92, 1:91, 1:90, 1:89, 1:88, 1:87, 1:86, 1:85, 1:84, 1:83, 1:82, 1:81, 1:80, 1:79, 1:78, 1:77, 1:76, 1:75, 1:74, 1:73, 1:72, 1:71, 1:70, 1:69, 1:68, 1:67, 1:66, 1:65, 1:64, 1:63, 1:62, 1:61, 1:60, 1:59, 1:58, 1:57, 1:56, 1:55, 1:54, 1:53, 1:52, 1:51, 1:50, 1:49, 1:48, 1:47, 1:46, 1:45, 1:44, 1:43, 1:42, 1:41, 1:40, 1:39, 1:38, 1:37, 1:36, 1:35, 1:34, 1:33, 1:32, 1:31, 1:30, 1:29, 1:28, 1:27, 1:26, 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1 or any value between the two values, preferably 1:10 to 20:1, and more preferably 1:10 to 10:1. Some embodiments provide a pharmaceutical composition with a weight ratio of the absorption enhancer to abiraterone acetate of 1:2. Some embodiments provide a pharmaceutical composition with a weight ratio of the absorption enhancer to abiraterone acetate of 1:1. Some embodiments provide a pharmaceutical composition with a weight ratio of the absorption enhancer to abiraterone acetate of 2:1.

In other embodiments, the pharmaceutical composition further comprises lactose. In some embodiments, the lactose is present in an amount of 15 to 80% by weight, and may be 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80% by weight or any value between the two values, more preferably 25 to 75%, such as 37%, 37.5% or 38% by weight, relative to the total weight of the pharmaceutical composition.

Further, the pharmaceutical composition of the present disclosure further comprises a disintegrant, wherein the disintegrant is at least one selected from the group consisting of croscarmellose sodium, crospovidone, sodium carboxymethyl starch, calcium carboxymethylcellulose, low-substituted hydroxypropyl cellulose, starch, pregelatinized starch and alginic acid. Preferably, the disintegrant is present in an amount of 0.5 to 20% by weight, and may be 0.5%, 06%, 0.7%, 0.8%, 0.9%, 1.0%, 1.1%, 1.3%, 1.5%, 1.7%, 1.9%, 2.1%, 2.3%, 2.5%, 2.7%, 2.9%, 3.1%, 3.3%, 3.5%, 3.7%, 3.9%, 4.1%, 4.3%, 4.5%, 4.7%, 4.9%, 5.1%, 5.3%, 5.5%, 5.7%, 5.9%, 6.1%, 6.3%, 6.5%, 6.7%, 6.9%, 7.1%, 7.3%, 7.5%, 7.7%, 7.9%, 8.1%, 8.3%, 8.5%, 8.7%, 8.9%, 9.1%, 9.3%, 9.5%, 9.7%, 9.9%, 10.1%, 10.3%, 10.5%, 10.7%, 10.9%, 11.1%, 11.3%, 11.5%, 11.7%, 11.9%, 12.1%, 12.3%, 12.5%, 12.7%, 12.9%, 13.1%, 13.3%, 13.5%, 13.7%, 13.9%, 14.1%, 14.3%, 14.5%, 14.7%, 14.9%, 15.1%, 15.3%, 15.5%, 15.7%, 15.9%, 16.1%, 16.3%, 16.5%, 16.7%, 16.9%, 17.1%, 17.3%, 17.5%, 17.7%, 17.9%, 18.1%, 18.3%, 18.5%, 18.7%, 18.9%, 19.1%, 19.3%, 19.5%, 19.7%, 19.9%, 20% by weight or any value between the two values, more preferably 2 to 10%, such as 7% or 8% by weight, relative to the total weight of the pharmaceutical composition.

In another aspect, the pharmaceutical composition of the present disclosure further comprises at least one stabilizer selected from the group consisting of cellulose derivatives and surfactants, wherein the cellulose derivative is preferably hydroxypropyl methyl cellulose, methyl cellulose, hydroxypropyl cellulose, hydroxyethyl cellulose or sodium carboxymethyl cellulose; the surfactant is preferably polyoxyethylene ether, poloxamer, polyethylene glycol glyceride, polyoxyethylenated castor oil or polyethoxylated hydrogenated castor oil, sodium lauryl sulfate or sodium cholate.

In some embodiments, the stabilizer is one or more selected from the group consisting of hydroxypropyl methyl cellulose, hydroxypropyl cellulose, sodium lauryl sulfate and poloxamer.

Further, the pharmaceutical composition comprises at least two or more stabilizers.

In some embodiments, the stabilizer is preferably hydroxypropyl methyl cellulose or sodium lauryl sulfate.

In another aspect, the particle size of abiraterone acetate in the pharmaceutical composition of the present disclosure can be expressed as a cumulative particle size distribution percentage, such as D90 or D50. The term "D50" refers to the corresponding particle size when the cumulative particle size distribution percentage of a sample reaches 50%. The term "D90" refers to the corresponding particle size when the cumulative particle size distribution percentage of a sample reaches 90%. The term "D10" in the present invention refers to the corresponding particle size when the cumulative particle size distribution percentage of a sample reaches 10%.

The D90 value of the abiraterone acetate particles in the pharmaceutical composition provided by some embodiments is not greater than 1000 nm or less, including but not limited to not greater than 1000 nm, not greater than 900 nm, not greater than 800 nm, not greater than 700 nm, not greater than 600 nm, not greater than 500 nm, not greater than 400 nm, not greater than 300 nm or less, or a value between any two values.

In some embodiments, the D90 value of abiraterone acetate in the pharmaceutical composition is 400 to 600 nm, and may be 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, 600 nm or any value between the two values. In some embodiments, the D90 value of abiraterone acetate in the pharmaceutical composition is 450 nm.

The D50 value of abiraterone acetate in the pharmaceutical composition provided by some embodiments is not greater than 500 nm or less, including but not limited to not greater than 500 nm, not greater than 400 nm, not greater than 300 nm, not greater than 200 nm or less, or a value between any two values.

In some embodiments, the D50 value of abiraterone acetate in the pharmaceutical composition is 150 to 300 nm, and may be 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm or a value between any two values. In some embodiments, the D50 value of abiraterone acetate in the pharmaceutical composition is 230 nm.

The D10 value of abiraterone acetate in the pharmaceutical composition provided by some embodiments is not greater than 200 nm or less, including but not limited to not greater than 150 nm, not greater than 100 nm or less, or a value between any two values.

In some embodiments, the D10 value of abiraterone acetate in the pharmaceutical composition is 50 to 120 nm, and may be 50 nm, 55 nm, 60 nm, 65 nm, 70 nm, 75 nm, 80 nm, 85 nm, 90 nm, 95 nm, 100 nm, 110 nm, 120 nm, or a value between any two values. In some embodiments, the D10 value of abiraterone acetate in the pharmaceutical composition is 99 nm. In some embodiments, the D10 value of abiraterone acetate in the pharmaceutical composition is 110 nm. In some embodiments, the D10 value of abiraterone acetate in the pharmaceutical composition is 120 nm.

In another aspect, the particle size of abiraterone acetate in the pharmaceutical composition of the present disclosure can be expressed as average particle size, which is not greater than 500 nm or less. The term "average particle size" (Z-average Size), for example, "average particle size of less than 500 nm" is the average light intensity, which is calculated from the light intensity contributed by different types of particles. The person skilled in the art can determine the average particle size of the particles by well-known and conventional particle size measurement techniques. Such techniques include, for example, sedimentation field flow fractionation, photon correlation spectroscopy, light scattering and the like.

In some embodiments, the average particle size of abiraterone acetate in the pharmaceutical composition is not greater than 500 nm. In some embodiments, the average particle size of abiraterone acetate in the pharmaceutical composition is not greater than 400 nm. In some embodiments, the average particle size of abiraterone acetate in the pharmaceutical composition is not greater than 300 nm, and may be 300 nm, 295 nm, 290 nm, 285 nm, 280 nm, 275 nm, 270 nm, 265 nm, 260 nm, 255 nm, 250 nm, 245 nm, 240 nm, 235 nm, 230 nm, 225 nm, 220 nm, 215 nm, 210 nm, 205 nm, 200 nm, 195 nm, 190 nm, 185 nm, 180 nm, 175 nm, 170 nm, 165 nm, 160 nm, 155 nm, 150 nm, 145 nm, 140 nm, 135 nm, 130 nm, 125 nm, 120 nm, 115 nm, 110 nm, 105 nm, 100 nm or less or any value between the two values. In some embodiments, the average particle size of the abiraterone acetate particles in the pharmaceutical composition is not greater than 215 nm.

In another aspect, the pharmaceutical composition of the present disclosure substantially comprise no microcrystalline cellulose.

The pharmaceutical composition of the present disclosure comprises:
a) 150 mg of abiraterone acetate,
b) 10 to 40% by weight of an absorption enhancer, wherein the absorption enhancer is preferably at least one of 8-(salicylamido)caprylic acid and sodium 8-(salicylamido)caprylate, and
c) 0.5 to 20% by weight of a stabilizer, wherein the stabilizer is preferably at least one of hydroxypropyl methyl cellulose and sodium lauryl sulfate.

Further, the pharmaceutical composition of the present disclosure comprises:
a) 150 mg of abiraterone acetate,
b) 10 to 40% by weight of an absorption enhancer, wherein the absorption enhancer is preferably at least one of 8-(salicylamido)caprylic acid and sodium 8-(salicylamido)caprylate,
c) 0.5 to 20% by weight of a stabilizer, wherein the stabilizer is preferably at least one of hydroxypropyl methyl cellulose and sodium lauryl sulfate, and
d) 25 to 75% by weight of lactose.

Further, the pharmaceutical composition of the present disclosure comprises:
a) 150 mg of abiraterone acetate,
b) 10 to 40% by weight of an absorption enhancer, wherein the absorption enhancer is preferably at least one of 8-(salicylamido)caprylic acid and sodium 8-(salicylamido)caprylate,
c) 0.5 to 20% by weight of a stabilizer, wherein the stabilizer is preferably at least one of hydroxypropyl methyl cellulose and sodium lauryl sulfate,
d) 25 to 75% by weight of lactose, and
e) 0.5 to 20% by weight of a disintegrant.

In some embodiments, the pharmaceutical composition further comprises 0.1 to 2.0% by weight of lubricant.

Further, the lubricant is known or can be determined by the person skilled in the art, and is selected, but is not limited to, at least one of magnesium stearate, stearic acid, palmitic acid, calcium stearate, talc, colloidal silica, carnauba wax and sodium stearyl fumarate; preferably, the lubricant described in the present disclosure is present in an amount of 0.1 to 5% by weight, and may be 0.1%, 0.2%, 0.3%, 0.4%, 0.5%, 0.6%, 0.7%, 0.8%, 0.9%, 1%, 1.1%, 1.3%, 1.5%, 1.7%, 1.9%, 2.1%, 2.3%, 2.5%, 2.7%, 2.9%, 3.1%, 3.3%, 3.5%, 3.7%, 3.9%, 4.1%, 4.3%, 4.5%, 4.7%, 4.9%, 5.0% by weight or any value between the two values, preferably 0.1 to 2.0% by weight, relative to the total weight of the pharmaceutical composition.

The present disclosure also provide another pharmaceutical composition, wherein the mean blood plasma $C_{max}$ is up to 3 times that of the fasting state upon orally administering 300 mg dose of abiraterone acetate to a group of healthy male subjects in the high-fat state (total calories about 800 to 1000 kcal, of which about 50% of the calories come from fat).

In other embodiments, the mean blood plasma $AUC_{0-t}$ is up to 3 times that of the fasting state, and may be 3.0 times, 2.8 times, 2.6 times, 2.4 times, 2.2 times, 2.0 times, 1.8 times, 1.6 times, 1.4 times, 1.2 times, 1.0 times or less or any value between the two values that of the fasting state, upon orally administering 300 mg dose of abiraterone acetate to a group of healthy male subjects in the high-fat state (total calories about 800 to 1000 kcal, of which about 50% of the calories come from fat).

In other embodiments, the mean blood plasma $AUC_{0-\infty}$ is up to 3 times that of the fasting state, and may be 3.0 times, 2.8 times, 2.6 times, 2.4 times, 2.2 times, 2.0 times, 1.8 times, 1.6 times, 1.4 times, 1.2 times, 1.0 times or less or any value between the two values that of the fasting state, upon orally administering 300 mg dose of abiraterone acetate to a group of healthy male subjects in the high-fat state (total calories about 800 to 1000 kcal, of which about 50% of the calories come from fat).

In another aspect, the present disclosure also provides a pharmaceutical composition, wherein the intra-individual coefficient of variation (CV) of the mean blood plasma $AUC_{0-t}$ of abiraterone is less than 25% or less upon orally administering 300 mg dose of abiraterone acetate to a group of healthy male subjects in a fasting state The provided intra-individual coefficient of variation (CV) of the mean blood plasma $AUC_{0-t}$ of abiraterone may be 25%, 24%, 23%, 22%, 21%, 20%, 19%, 18%, 17%, 16%, 15%, 14%, 13%, 12%, 11%, 10%, 9%, 8%, 7%, 6%, 5% or less or any value between the two values. In some embodiments, the intra-individual coefficient of variation (CV) of the mean blood plasma $AUC_{0-t}$ of abiraterone is about 15%, upon administering 300 mg dose of abiraterone acetate to a group of healthy male subjects in the fasting state.

In another aspect, the present disclosure also provides a pharmaceutical composition, wherein the intra-individual coefficient of variation (CV) of the mean blood plasma $AUC_{0-\infty}$ of abiraterone is less than 25% or less upon orally administering 300 mg dose of abiraterone acetate to a group of healthy male subjects in a fasting state. The provided intra-individual coefficient of variation (CV) of the mean blood plasma $AUC_{0-\infty}$ of abiraterone may be 25%, 24%, 23%, 22%, 21%, 20%, 19%, 18%, 17%, 16%, 15%, 14%, 13%, 12%, 11%, 10%, 9%, 8%, 7%, 6%, 5% or less or any value between the two values. In some embodiments, the intra-individual coefficient of variation (CV) of the mean blood plasma $AUC_{0-\infty}$ of abiraterone is about 15% upon orally administering 300 mg dose of abiraterone acetate to a group of healthy male subjects in a fasting state.

In another aspect, the present disclosure also provides a pharmaceutical composition, wherein the intra-individual coefficient of variation (CV) of the mean blood plasma $AUC_{0-\infty}$ is reduced by at least 5% or more, compared to the 1000 mg dose of Zytiga®, upon orally administering 300 mg dose of abiraterone acetate to a group of healthy male subjects in a fasting state. The provided intra-individual coefficient of variation (CV) of the mean blood plasma $AUC_{0-\infty}$ is reduced by at least 5%, 6%, 7%, 8%, 9%, 10%, 11%, 12%, 13%, 14%, 15%, 16%, 17%, 18%, 19%, 20% or more or any value between the two values.

In some embodiments, the intra-individual coefficient of variation (CV) of the mean blood plasma $AUC_{0-\infty}$ provided by the 300 mg dose of the abiraterone acetate pharmaceutical composition is reduced by 11% compared to the 1000 mg dose of Zytiga®.

In another aspect, the present disclosure also provides a pharmaceutical composition, wherein the intra-individual coefficient of variation (CV) of the mean blood plasma $AUC_{0-t}$ is reduced by at least 5% or more compared to the 1000 mg dose of Zytiga®, upon orally administering 300 mg dose of abiraterone acetate to a group of healthy male subjects in a fasting state, provides. The provided intra-individual coefficient of variation (CV) of the mean blood plasma $AUC_{0-t}$ is reduced by at least 5%, 6%, 7%, 8%, 9%, 10%, 11%, 12%, 13%, 14%, 15%, 16%, 17%, 18%, 19%, 20% or more or any value between the two values.

In some embodiments, the intra-individual coefficient of variation (CV) of the mean blood plasma $AUC_{0-t}$ provided by the 300 mg dose of the abiraterone acetate pharmaceutical composition is reduced by 11% compared to the 1000 mg dose of Zytiga®.

In another aspect, the present disclosure also provides a pharmaceutical composition comprising abiraterone acetate, an absorption enhancer and lactose, preferably the lactose is present in an amount of 15 to 80%, and more preferably 25 to 75%, such as 37%, 37.5% or 38% by weight, relative to the total weight of the pharmaceutical composition. In some embodiments, the pharmaceutical composition comprises 150 mg of abiraterone acetate. Further, some embodiments provide a pharmaceutical composition comprising other excipients such as one or more of disintegrants, stabilizers or lubricants. The types of the excipients are well known to the person skilled in the art, as described in the aforementioned pharmaceutical compositions.

In another aspect, the present disclosure also provides a pharmaceutical composition comprising abiraterone acetate and an absorption enhancer which substantially comprise no microcrystalline cellulose. Further, some embodiments provide a pharmaceutical composition comprising other excipients such as one or more of fillers, stabilizers or lubricants. The types of excipients are well known to the person skilled in the art, as described in the aforementioned pharmaceutical compositions.

The present disclosure also provides a method for preparing the aforementioned pharmaceutical composition, comprising the step of mixing abiraterone acetate with an absorption enhancer and optionally at least one excipient, wherein the excipient is at least one selected from the group consisting of lactose and disintegrants.

In some embodiments, the method for preparing the aforementioned pharmaceutical composition comprises the steps of preparing a nanosuspension of abiraterone acetate, adding an absorption enhancer and optionally at least one excipient such as lactose, and mixing them.

In some embodiments, the steps of preparing the nanosuspension of abiraterone or its derivatives according to the present disclosure include the following steps or refer to the preparation process in WO2014009436, and the relevant content is incorporated herein:

in some embodiments, the method comprises the step of preparing a nanosuspension of abiraterone acetate, namely:
a) preparing a suspension of abiraterone acetate in a liquid solvent, wherein the liquid solvent is selected from the group consisting of water, polyethylene glycol, glycerin, propylene glycol or any combination thereof, preferably water; b) adding grinding balls to the suspension of step a) to obtain a slurry for grinding; and c) grinding the slurry to obtain the nanosuspension with particle size D90 value less than 500 nm.

Further, the step a) includes a stabilizer, and the stabilizer is preferably selected from the group consisting of hydroxypropyl methyl cellulose and sodium lauryl sulfate.

Further, the aforementioned nanosuspension is further processed and converted into a concentrated nanosuspension.

In some embodiments, at least part of the solvent is removed by conventional drying methods such as freeze drying or spray drying to obtain a concentrated nanosuspension.

In some embodiments, fluidized bed granulation is used to remove solvent from the nanosuspension to obtain a concentrated nanosuspension.

In some embodiments, the method for preparing the aforementioned pharmaceutical composition comprises the steps of preparing a nanosuspension of abiraterone acetate, adding an absorption enhancer and optionally at least one excipient such as lactose, mixing them and granulating through a fluidized bed.

In other embodiments, the method for preparing the aforementioned pharmaceutical composition comprises the steps of:
a) preparing the nanosuspension of abiraterone acetate according to the aforementioned method,
b) adding an absorption enhancer and optionally at least one excipient such as lactose,
c) granulating the nanosuspension obtained in step b) through a fluidized bed.

In another aspect, the particle size of the active ingredient abiraterone acetate particles used in the present disclosure is measured by the screening method, and it is preferably (but not necessarily) less than 100 μm. If the particle size of the active ingredient particles is greater than 100 μm, it is preferred to reduce the particle size to below 100 μm by a conventional grinding method such as an air jet mill or a crushing mill.

The selected active ingredient raw material can be added to a liquid medium in which it is essentially insoluble, preferably such as water, to form an initial mixture. The concentration of the active ingredient in the liquid medium is 0.1 to 60% (W/W), preferably 5 to 30% (W/W), and may be 5, 6, 7, 8, 9, 10, 11, 12, 13, 14, 15, 16, 17, 18, 19, 20, 21, 22, 23, 24, 25, 26, 27, 28, 29, 30% (W/W). It is preferred if the stabilizer is present in the initial mixture, but this is not necessary. The apparent viscosity of the initial mixture suspension is preferably less than 2000 centipoise.

The average particle size of the initial mixture can be directly reduced to below 5000 nm in the dispersed phase by mechanical means. When grinding with a ball mill, it is preferred to directly apply the initial mixture. Another method is to disperse the active ingredient and optional surface stabilizer in a liquid medium by a suitable method, such as a roller mill or a Cowles-type mixer, until a uniform dispersion system with no large clumps visible to the naked eye is formed. If a circulating media mill is used for grinding, it is preferred to subject the preliminary mixture to this pre-grinding and dispersion step.

The conventional mechanical means used to prepare the nano-scale particle size of the active ingredient can be a suitable dispersion mill including a ball mill, an attritor, a vibration mill, a planetary mill, and a media mill (such as a sand mill and a bead mill).

The grinding medium used in the step of grinding particles can be rigid media, preferably spherical or granular, with an average particle size of less than 3 mm, and more preferably less than 1 mm. This medium has a shorter processing time and less wear on the grinding equipment, and at the same time can provide the particles of the present disclosure. The raw material selection of the grinding media is not important. For example, zirconium oxide, 95% ZrO stabilized with magnesium, zirconium silicate, and glass grinding media can provide particles within the allowable impurity content range for the preparation of pharmaceutical complexes. Furthermore, other media such as stainless steel, titanium dioxide, and aluminum oxide can also be used. Preferably, the density ratio of the medium is greater than 2.5 g/cm$^3$.

The grinding time varies greatly, mainly depending on the specific mechanical methods and processing conditions. For ball mills, the processing time can take 1 day or longer. In another aspect, processing times of less than one day (retention times ranging from one minute to several hours) with high-shear media mills have provided the desired results.

The process of crushing the particles must be carried out at a temperature at which the active ingredient does not degrade significantly. It is generally preferred to process at temperatures below 50° C. If necessary, the processing equipment can be cooled with conventional cooling equipment. These particle production technologies are well-known to the person skilled in the art. For detailed grinding, wet grinding, homogenization, precipitation, supercritical fluid particle production technologies and the like, please refer to CN1063630C, CN101175481A or CN1515244A, and the relevant contents are specifically incorporated into the present application.

Further, the method according to the present disclosure also comprises the steps of granulating, tableting, coating or filling capsules.

The present disclosure also provides a use of the aforementioned pharmaceutical composition in the preparation of a medicament for treating prostate cancer. Further, the aforementioned pharmaceutical composition is used in combination with a glucocorticoid, preferably prednisone, prednisolone or methylprednisolone.

In another aspect, the present disclosure also provides a method for treating prostate cancer, comprising administering the aforementioned pharmaceutical composition at a daily dose of 300 mg. Further, the aforementioned method also comprises administering a glucocorticoid, preferably prednisone, prednisolone or methylprednisolone.

In some embodiments, a mean blood plasma $C_{max}$ of 209±142 ng/ml is provided upon orally administering 300 mg dose of abiraterone acetate to a group of healthy male subjects in a fasting state.

In some embodiments, a median $T_{max}$ of 1 hour is provided upon orally administering 300 mg dose of abiraterone acetate to a group of healthy male subjects in a fasting state.

In some embodiments, a mean blood plasma $AUC_{0-t}$ of 620.08±370.19 ng·h/ml is provided upon orally administering 300 mg dose of abiraterone acetate to a group of healthy male subjects in a fasting state.

In some embodiments, a mean blood plasma $AUC_{0-\infty}$ of 627.60±370.44 ng·h/ml is provided upon orally administering 300 mg dose of abiraterone acetate to a group of healthy male subjects in a fasting state.

In another aspect, 80 to 125% of the mean blood plasma $C_{max}$ of 209 ng/ml is provided upon orally administering 300 mg dose of abiraterone acetate to a group of healthy male subjects in a fasting state.

In some embodiments, 80 to 125% of the mean blood plasma $AUC_{0-t}$ of 620.08 ng·h/ml is provided upon orally administering 300 mg dose of abiraterone acetate to a group of healthy male subjects in a fasting state.

In some embodiments, 80 to 125% of the mean blood plasma $AUC_{0-\infty}$ of 627.60 ng·h/ml is provided upon orally administering 300 mg dose of abiraterone acetate to a group of healthy male subjects in a fasting state.

In some embodiments, the mean blood plasma $C_{max}$ is up to 3 times that of the fasting state upon administering 300 mg dose of abiraterone acetate to a group of healthy male subjects in the high-fat state (total calories about 800 to 1000 kcal, of which about 50% of the calories come from fat).

In other embodiments, the mean blood plasma $AUC_{0-t}$ is up to 3 times that of the fasting state, and may be 3.0 times, 2.8 times, 2.6 times, 2.4 times, 2.2 times, 2.0 times, 1.8 times, 1.6 times, 1.4 times, 1.2 times, 1.0 times or less or any value between the two values that of the fasting state, upon orally administering 300 mg dose of abiraterone acetate to a group of healthy male subjects in the high-fat state (total calories about 800 to 1000 kcal, of which about 50% of the calories come from fat).

In other embodiments, the mean blood plasma $AUC_{0-\infty}$ is up to 3 times that of the fasting state, and may be 3.0 times, 2.8 times, 2.6 times, 2.4 times, 2.2 times, 2.0 times, 1.8 times, 1.6 times, 1.4 times, 1.2 times, 1.0 times or less or any value between the two values that of the fasting state, upon orally administering 300 mg dose of abiraterone acetate to a group of healthy male subjects in the high-fat state (total calories about 800 to 1000 kcal, of which about 50% of the calories come from fat).

In some embodiments, the intra-individual coefficient of variation (CV) of the mean blood plasma $AUC_{0-\infty}$ of abiraterone provided by 300 mg dose of the abiraterone acetate composition in combination with prednisone is less than 25% or less, and may be 25.0%, 24.5%, 24.0%, 23.5%, 23.0%, 22.5%, 22.0%, 21.5%, 21.0%, 20.5%, 20.0%, 19.5%, 19.0%, 18.5%, 18.0%, 17.5%, 17.0%, 16.5%, 16.0%, 15.5%, 15.0%, 14.5%, 14.0%, 13.5%, 13.0%, 12.5%, 12.0%, 11.5%, 11.0%, 10.5%, 10.0% or less or any value between the two values. In some embodiments, the intra-individual coefficient of variation (CV) of the mean blood plasma $AUC_{0-\infty}$ of abiraterone is about 15% upon orally administering 300 mg dose of abiraterone acetate to a group of healthy male subjects in a fasting state.

In some embodiments, the intra-individual coefficient of variation (CV) of the mean blood plasma $AUC_{0-t}$ of abiraterone provided by 300 mg dose of the abiraterone acetate composition in combination with prednisone is less than 25% or less, and may be 25.0%, 24.5%, 24.0%, 23.5%, 23.0%, 22.5%, 22.0%, 21.5%, 21.0%, 20.5%, 20.0%, 19.5%, 19.0%, 18.5%, 18.0%, 17.5%, 17.0%, 16.5%, 16.0%, 15.5%, 15.0%, 14.5%, 14.0%, 13.5%, 13.0%, 12.5%, 12.0%, 11.5%, 11.0%, 10.5%, 10.0% or less or any value between the two values. In some embodiments, the intra-individual coefficient of variation (CV) of the mean blood plasma $AUC_{0-t}$ of abiraterone is about 15% upon orally administering 300 mg dose of abiraterone acetate to a group of healthy male subjects in a fasting state.

In another embodiments, the intra-individual coefficient of variation (CV) of the mean blood plasma $AUC_{0-\infty}$ of abiraterone provided by 300 mg dose of the abiraterone acetate composition in combination with prednisone is reduced by at least 5% or more which may be 5.0%, 5.2%, 5.4%, 5.6%, 5.8%, 6.0%, 6.2%, 6.4%, 6.6%, 6.8%, 7.0%, 7.2%, 7.4%, 7.6%, 7.8%, 8.0%, 8.2%, 8.4%, 8.6%, 8.8%, 9.0%, 9.2%, 9.4%, 9.6%, 9.8%, 10.0%, 10.2%, 10.4%, 10.6%, 10.8%, 11.0%, 11.2%, 11.4%, 11.6%, 11.8%, 12.0%, 12.2%, 12.4%, 12.6%, 12.8%, 13.0%, 13.2%, 13.4%, 13.6%, 13.8%, 14.0%, 14.2%, 14.4%, 14.6%, 14.8%, 15.0% or more or any value between the two values compared to the 1000 mg dose of Zytiga®. In some embodiments, the intra-individual coefficient of variation (CV) of the mean blood plasma $AUC_{0-\infty}$ provided by 300 mg dose of the abiraterone acetate pharmaceutical composition is reduced by 11% compared to the 1000 mg dose of Zytiga®.

In other embodiments, the intra-individual coefficient of variation (CV) of the mean blood plasma $AUC_{0-t}$ of abiraterone provided by 300 mg dose of the abiraterone acetate composition in combination with prednisone is reduced by at least 5% or more, which may be 5.0%, 5.2%, 5.4%, 5.6%, 5.8%, 6.0%, 6.2%, 6.4%, 6.6%, 6.8%, 7.0%, 7.2%, 7.4%, 7.6%, 7.8%, 8.0%, 8.2%, 8.4%, 8.6%, 8.8%, 9.0%, 9.2%, 9.4%, 9.6%, 9.8%, 10.0%, 10.2%, 10.4%, 10.6%, 10.8%, 11.0%, 11.2%, 11.4%, 11.6%, 11.8%, 12.0%, 12.2%, 12.4%, 12.6%, 12.8%, 13.0%, 13.2%, 13.4%, 13.6%, 13.8%, 14.0%, 14.2%, 14.4%, 14.6%, 14.8%, 15.0% or more or any value between the two values compared to the 1000 mg dose of Zytiga®. In other embodiments, \the intra-individual coefficient of variation (CV) of the mean blood plasma $AUC_{0-t}$ provided by 300 mg dose of the abiraterone acetate pharmaceutical composition is recuded by 10% compared to the 1000 mg dose of Zytiga®.

Terms:

The term "average particle size" (Z-average Size) according to the present disclosure, for example, "average particle size of less than 1000 nm" is the average light intensity, which is calculated from the light intensity contributed by different types of particles. The person skilled in the art can determine the average particle size of the particles by well-known and conventional particle size measurement techniques. Such techniques include, for example, sedimentation field flow fractionation, photon correlation spectroscopy, light scattering and the like.

The term "polydispersity index" (PDI) according to the present disclosure reflects the uniformity of particle size and is an important index for particle size characterization.

The term "effective amount" or "therapeutically effective amount" according to the present disclosure encompasses an amount sufficient to ameliorate or prevent a symptom or sign of a medical condition. The term "effective amount" also refers to an amount sufficient to allow or facilitate diagnosis. An effective amount for a particular patient or veterinary subject may vary, depending on factors such as the condition to be treated, the general health of the patient, the route and dose of administration, and the severity of side effects. An effective amount can be the maximal dose or administration regimen that avoids significant side effects or toxic effects.

The term "substantially not comprise" or "substantially comprise no" according to the present disclosure, for example, the pharmaceutical composition substantially comprises no citric acid, means the citric acid is not added. It should be noted that, as long as it is determined that the stability of the pharmaceutical composition is not due to the added citric acid.

The term "total weight of pharmaceutical composition" described in the present disclosure refers to the weight of tablet core without coating agent, and is used to calculate the numerical range of the amount of active ingredients or other kinds of pharmaceutical excipients.

The values disclosed according to the present disclosure are Instrumental values which have certain degree of error. Generally speaking, ±10% are within the reasonable error range. There is a certain degree of error variation depending on the context in which it is used. The error variation does not exceed ±10%, which may be ±9%, ±8%, ±7%, ±6%, ±5%, ±4%, ±3%, ±2% or ±1%, preferably ±5%. For example, the amount of lactose in the pharmaceutical composition provided by some embodiments varies to a certain extent due to the existence of errors, usually ±10%. The particle size D90 of abiraterone acetate in the drugs provided by some embodiments also has a certain degree of measurement change, usually ±10%.

Pharmacokinetic Parameters

| Parameters | Meanings |
|---|---|
| $C_{max}$ | Peak concentration obtained directly according to the measured data of blood concentration-time. |
| $AUC_{0-t}$ | Area under the plasma drug concentration - time curve from time 0 to the last measurable concentration, which is calculated by the linear trapezoid rule: $AUC_{(i, i+1)} = (T_{i+1} - T_i)(C_i + C_{i+1})/2$; wherein $AUC_{0-t}$ is the sum of all $AUC_{(i, i+1)}$. |
| $AUC_{0-\infty}$ | Area under the plasma drug concentration - time curve from time 0 to infinity. $AUC_{0-\infty} = AUC_{0-t} + C_t/\lambda_z$ ($C_t$ is the last measurable plasma drug concentration). |
| $T_{max}$ | Time to peak concentration obtained directly according to the measured data of blood concentration-time. |
| $\lambda_z$ | Elimination rate constant which is the opposite number of the slope at the terminal segment of the semilog plasma drug concentration-time curve, calculated by linear regression method. |
| $t_{1/2z}$ | Terminal elimination half-life. $t_{1/2z} = \ln2/\lambda_z$. |
| $AUC\_\%\ Extrap$ | Percentage of residual area. $AUC\_\%\ Extrap = [(AUC_{0-\infty} - AUC_{0-t})/AUC_{0-\infty}] \times 100\%$ |
| $V_z/F$ | Apparent volume of distribution. $V_z/F = CL_z/F/\lambda_z$. |
| $CL_z/F$ | Apparent clearance rate. $CL_z/F = Dose/AUC_{0-\infty}$. |
| $MRT_{0-t}$ | Mean retention time from time 0 to the time of minimum detectable plasma drug concentration. $MRT_{0-t} = AUMC_{0-t}/AUC_{0-t}$ |
| $MRT_{0-\infty}$ | Mean retention time from time 0 extrapolated to infinity. $MRT_{0-\infty} = AUMC_{0-\infty}/AUC_{0-\infty}$. |
| CV % | Coefficient of Variation |

Pharmacokinetic Evaluation Index:

The non-compartmental model (NCA) is used to calculate the pharmacokinetic parameters of abiraterone acetate, SNAC, prednisone and prednisolone. The main pharmacokinetic parameters include $T_{max}$, $C_{max}$, $AUC_{0-t}$, $AUC_{0-\infty}$, $t_{1/2z}$, $CL_z$ ($CL_z/F$), $V_z$ ($V_z/F$), $\lambda_z$, $MRT_{0-t}$, $MRT_{0-\infty}$ and $AUC\_\%$ Extrap.

1) The pharmacokinetic parameters $AUC_{0-t}$, $AUC_{0-\infty}$ and $C_{max}$ of abiraterone acetate are statistically analyzed, and the intra-individual standard deviation SWR of the pharmacokinetic parameters AUC and $C_{max}$ of the reference formulation is calculated respectively.

If SWR<0.294, the main pharmacokinetic parameters are logarithmically transformed and then subjected to multi-factor analysis of variance (ANOVA) for significance testing, and the statistical analysis method of 90% confidence interval is used to evaluate and judge the relative bioavailability of drugs.

If SWR≥0.294, the main pharmacokinetic parameters are logarithmically transformed and then subjected to analysis of variance (ANOVA) for significance testing, and then evaluated by the mean bioavailability corrected by the reference formulation. The upper limit of the 95% confidence interval of $(\overline{Y_T}-\overline{Y_R})^2-\theta\ S^2_{WR}$ is calculated, wherein the corrected BE limit $$\theta = \left(\frac{\ln(1.25)}{\sigma_{w0}}\right)^2,$$

the prescribed limit σw0 is 0.25, and meanwhile the point estimate for geometric mean ratio is calculated.

2) The pharmacokinetic parameters $AUC_{0-t}$, $AUC_{0-\infty}$ and $C_{max}$ of prednisone and prednisolone in the test formulation group and the reference formulation group are calculated respectively. The main pharmacokinetic parameters are logarithmically transformed and then subjected to multi-factor analysis of variance (ANOVA) for significance testing, and then the statistical analysis methods of two one-side t-test and calculating 90% confidence interval are used to evaluate the effect of SNAC on the pharmacokinetics of prednisone in combination with the active metabolite prednisolone.

The reference formulation R according to the present disclosure is a commercially available abiraterone acetate ordinary tablet (trade name Zytiga®).

The pharmaceutical excipients or reagents according to the present disclosure can all come from commercial sources, for example, hydroxypropyl methylcellulose is commercially available. Abiraterone acetate can be prepared by referring to the method described in the examples of CN101528308.

DETAIL DESCRIPTION OF THE INVENTION

The present disclosure will be further described in detail with reference to the following examples. These examples are only for the purpose of illustration and should not be considered as limiting the scope of the present disclosure.

Example 1

|  | Formulation 1 | Contents (mg) |
|---|---|---|
| Nanosuspension | Abiraterone acetate | 150 |
|  | Hydroxypropyl methylcellulose E5 LV | 38.6 |
|  | Sodium dodecyl sulfate | 3.85 |
|  | water | 1479.3 |
| Preparation | Lactose | 240.00 |
|  | Crosslinked povidone XL | 48.00 |
|  | Sodium 8-(salicylamido)caprylate | 150.00 |
|  | Magnesium stearate | 12.736 |

1) Preparation of Nanosuspension 19.2 g of HPMC E5 LV was dispersed and dissolved in 739.6 g of water, and then 1.92 g of SDS was dissolved in it. 75 g of abiraterone acetate was then added to the above solution followed by stirring and dispersion.

The sand mill (the volume of grinding chamber is 160 ml and filled with 112 ml of 0.3 mm grinding beads, the feeding speed is 160 rpm, and the grinding speed is 3000 rpm) was equipped. The dispersed suspension was added into the formulation tank of the sand mill, and grinded under stirring to obtain the nanosuspension of abiraterone acetate with D90 about 500 nm.

2) Fluid-Bed Granulation 105 g of absorption enhancer SNAC was added into 1170.2 g of the nanosuspension above, and then stirred for dispersion. 168 g of lactose and 33.6 g of cross-linked povidone XL were added into the fluidized bed for fluidized bed top spray granulation. After granulation, the granules were dried untile the moisture content of the particles was less than 2%.

3) Tabletting

The granules prepared by fluid-bed were mixed with magnesium stearate and then tableted to obtain 150 mg of big tablet.

In Vitro Dissolution Test

The dissolution test was carried out with the reference preparation (250 mg) and ½ tablet of the reference preparation (containing 125 mg of abiraterone acetate) according to the second method of dissolution determination (paddle method) in Chinese Pharmacopoeia (2015 Edition). 900 ml of phosphate buffer solution with pH6.8 containing 0.25% SDS was used as the dissolution medium. The specific dissolution rate data are shown in table 1 below.

TABLE 1

| Time (min) | Complete tablet of reference preparation (%) | 1/2 tablet of reference preparation (%) | Formulation 1 (%) |
|---|---|---|---|
| 5 | 4.6 | 7 | 11 |
| 10 | 10.1 | 17 | 24 |
| 15 | 17.7 | 30 | 37 |
| 20 | 24.3 | 41 | 48 |
| 25 | 30.1 | 50 | 58 |
| 30 | / | 56 | 68 |
| 45 | 44.8 | 68 | 90 |
| 60 | 51.1 | 74 | 98 |

Note:
Reference preparation R (commercial name Zytiga ®) 250 mg tablet.

Example 2

The formulations of table 2 were prepared according to the method described in Example 1.

TABLE 2

|  | Formulation 2 | | Formulation 3 | | Formulation 4 | |
|---|---|---|---|---|---|---|
|  | mg/tablet | Ratio (%) | mg/tablet | ratio (%) | mg/tablet | ratio (%) |
| Abiraterone Acetate | 150.000 | 23.56 | 150.000 | 23.56 | 150.000 | 19.79 |
| Hydroxypropyl methylcellulose E5 LV | 38.462 | 6.04 | 38.462 | 6.04 | 38.462 | 5.07 |
| Sodium dodecyl sulfate | 3.846 | 0.60 | 3.846 | 0.60 | 3.846 | 0.51 |
| sodium 8-(salicylamido)caprylate | 150.000 | 23.56 | 150.000 | 23.56 | 150.000 | 19.79 |
| lactose | 240.000 | 37.69 | 160.000 | 25.13 | 240.000 | 31.66 |
| Microcrystalline cellulose 102 | N/A | N/A | 80.000 | 12.56 | 120.000 | 15.83 |
| Crosslinked povidone XL | 48.000 | 7.54 | 48.000 | 7.54 | 48.000 | 6.33 |
| Magnesium stearate | 6.495 | 1.02 | 6.495 | 1.02 | 7.732 | 1.02 |
| Total weight | 636.803 | 100.01 | 636.803 | 100.01 | 758.040 | 100.00 |

In Vitro Dissolution Test

The dissolution test was carried out with Formulation 2, 3 and 4 according to the second method of dissolution determination (paddle method) in Chinese Pharmacopoeia (2015 Edition). 900 ml of phosphate buffer solution with pH6.8 containing 0.25% SDS was used as the dissolution medium. The specific dissolution rate data are shown in table below.

TABLE 3

| | Dissolution (%) | | | | | |
|---|---|---|---|---|---|---|
| | Formulation 2 | | Formulation 3 | | Formulation 4 | |
| Time (min) | API | SNAC | API | SNAC | API | SNAC |
| 5 min | 10 | 11 | 7 | 8 | 11 | 12 |
| 10 min | 22 | 23 | 14 | 16 | 22 | 24 |
| 15 min | 34 | 35 | 23 | 25 | 34 | 36 |
| 20 min | 46 | 46 | 32 | 33 | 45 | 47 |
| 25 min | 56 | 56 | 39 | 41 | 55 | 57 |
| 30 min | 65 | 65 | 46 | 48 | 64 | 66 |
| 45 min | 84 | 85 | 62 | 64 | 83 | 85 |
| 60 min | 95 | 95 | 74 | 76 | 92 | 94 |

Note:
API is the active ingredient abiraterone acetate, and the SNAC is sodium 8 - (salicylamido).

Results: the dissolution of the composition comprising lactose is better when comparing formulation 2 with formulation 3, and the dissolution of the composition comprising microcrystalline cellulose is slower. Moreover, compared with formulation 2, the amount of lactose for formulation 4 is unchanged, but the amount of microcrystalline cellulose is increased and the tablet weight is also increased. However, the dissolution of the two has no significant difference. The above results show that the addition of microcrystalline cellulose has no effect on dissolution, but the addition of microcrystalline cellulose leads to the increase of tablet weight and tablet size, which affects the swallowing of patients.

Test Example 1

Pharmacokinetics Study of Formulation 2

Eight male cynomolgus monkeys were administered by single oral gavage, including 4 cycles, 5 days per cycle, 20 days in total (see Table 4 for the protocol).

TABLE 4

Pharmacokinetic protocol

| | | Administration | | | |
|---|---|---|---|---|---|
| Group | Number of animals Male | Test samples* | Dose (mg/animal) | Number of tablets | Administration route |
| Cycle I (Fasting before administration) | | | | | |
| 1 | 8 | T | 300 | 2 | PO |
| Cycle II (Fasting before administration) | | | | | |
| 1 | 8 | R | 1000 | 4 | PO |
| Cycle III (High fat diet before administration, HFD) | | | | | |
| 1 | 8 | T | 300 | 2 | PO |
| Cycle IV (High fat diet before administration, HFD) | | | | | |
| 1 | 8 | R | 1000 | 4 | PO |

*T refers to the Formulation 2, R referes to the reference preparation R(commercially available, trade name Zytiga ®), t = 24 h.

The animals in cycle I and II were fasted before administration, while the animals in cycle III and IV were given high-fat food before administration. Animals in cycle I and III were given 300 mg of Formulation 2 (2 tablets of abiraterone acetate, T, comprising 300 mg of abiraterone), while animals in cycle II and IV were given 1000 mg of reference preparation (4 tablets of abiraterone acetate Zytiga®, R). Blood samples were collected before administration or at 0.25, 0.5, 1, 1.5, 2, 2.5, 3, 4, 8, 12 and 24 hours after administration. The validated LC-MS/MS method was used to determine the concentrations of abiraterone and SNAC in plasma samples. Only abiraterone was detected for those given reference preparation, while abiraterone and SNAC were both detected for those given test formulations. The main pharmacokinetic parameters were calculated according to the concentrations of abiraterone and SNAC in plasma using Phoenix WinNonlin® 7.0 software. The main pharmacokinetic data of abiraterone in plasma in cycles I-IV are shown in Table 5, and the main pharmacokinetic data of SNAC in plasma in cycles I and III are shown in Table 6.

TABLE 5

Main pharmacokinetic parameters of abiraterone in plasma after administration for cycles I-IV (Mean ± SD, n = 8)

| | Cycle I | Cycle II | Cycle III | Cycle IV |
|---|---|---|---|---|
| $T_{1/2}$ (h) | 5.16 ± 1.43 | 6.98 ± 2.55 | 2.73 ± 0.45 | 4.18 ± 1.85 |
| $T_{max}$ (h) | 2.63 ± 1.09 | 5.31 ± 2.28 | 3.88 ± 0.35 | 4.38 ± 1.51 |
| $C_{max}$ (ng/ml) | 638.72 ± 446.43 | 279.24 ± 278.84 | 1318.03 ± 1222.55 | 2194.92 ± 1834.66 |
| $C_{max}$/Dose (ng/ml/mg) | 2.13 ± 1.49 | 0.28 ± 0.28 | 4.39 ± 4.08 | 2.19 ± 1.83 |
| $AUC_{(0-t)}$ (h*ng/ml) | 2878.79 ± 1887.91 | 2237.37 ± 2149.95 | 6693.37 ± 4588.85 | 17896.14 ± 17519.8 |
| $AUC_{(0-\infty)}$ (h*ng/ml) | 2936.88 ± 1891.39 | 2061.49 ± 1272.36 | 6713.8 ± 4589.14 | 19638.3 ± 18392.73 |
| $AUC_{(0-t)}$/Dose (h*ng/ml/mg) | 9.6 ± 6.29 | 2.24 ± 2.15 | 22.31 ± 15.3 | 17.9 ± 17.52 |

By fasting administration (cycles I and II), the pharmacokinetic parameters of 300 mg of Formulation 2 are 638.72±446.43 ng/ml for $C_{max}$, 2878.79±1887.91 h*ng/ml for $AUC_{(0-t)}$, 2.63 h for $T_{max}$ and 5.16 h for $T_{1/2}$, which are 1.29 times, 2.29 times, 0.50 times and 0.74 times of those of 1000 mg reference preparation, respectively. By high fat diet before administration (cycles III and IV), the pharmacokinetic parameters of 300 mg of Formulation 2 are 1318.03±1222.55 ng/ml for $C_{max}$ and 6693.37±4588.85 h*ng/ml for $AUC_{(0-t)}$, which are 0.60 times and 0.37 times of those of 1000 mg of reference preparation, respectively. Comparing the reference preparations under fasting and high fat diet before administration (cycles II and IV), the $C_{max}$ and $AUC_{(0-t)}$ of the abiraterone in the plasma of the male cynomolgus monkeys under high-fat diet are 7.86 and 8.00 times respectively of those under fasting state, showing significant food effect. Comparing the Formulation 2 under fasting and high fat diet before administration (cycles I and III), the $C_{max}$ and $AUC_{(0-t)}$ of the abiraterone in the plasma of the male cynomolgus monkeys under high-fat diet were 2.07 and 2.33 times respectively of those under fasting state, showing a certain food effect which is lower than that of the reference preparation.

TABLE 6

Main pharmacokinetic parameters of SNAC in plasma after administration for Cycles I and III (mean ± SD, n = 8)

| Cycles | $T_{1/2}$ h | $T_{max}$ h | $C_{max}$ ng/ml | $AUC_{(0-t)}$ h*ng/ml | $AUC_{(0-\infty)}$ h*ng/ml |
|---|---|---|---|---|---|
| Cycle 1 (Fasting) | 3.16 ± 0.93 | 0.72 ± 0.49 | 34165.76 ± 18040.59 | 40349.03 ± 10430.88 | 40945.21 ± 10605.42 |
| Cycle 3 (High Fat Diet) | 2.71 ± 0.74 | 2.88 ± 0.74 | 4656.97 ± 2395.17 | 18374.08 ± 5740.25 | 18727.86 ± 5619.06 |

The peak time of SNAC in the plasma of cynomolgus monkeys under fasting state is faster, and $T_{max}$ is 0.72±0.49 h, $C_{max}$ is 34165.76±18040.59 ng/ml, $AUC_{(0-24\ h)}$ is 40349.03±10430.88 h*ng/ml, while $T_{max}$ is 2.88±0.74 h, $C_{max}$ is 4656.97±2395.17 ng/ml and $AUC_{(0-24\ h)}$ is 18374.08±5740.25 h*ng/ml under high-fat state. $T_{max}$ of SNAC in cynomolgus monkeys after high-fat diet is prolonged, and $C_{max}$ and $AUC_{(0-24\ h)}$ are decreased. Considering SNAC as an acidic drug (PKA 5.0), it may be related to the increased PH value in gastrointestinal tract under high-fat state.

Conclusion: in male cynomolgus monkeys under fasting state in Cycles I and II, the unit dose exposure (AUC (0-t)/dose) of abiraterone in the plasma of Formulation 2 is 4.29 times that of reference preparation, which improves the bioavailability of abiraterone significantly. The effect of high-fat diet on the exposure (AUC (0-t)) and $C_{max}$ of 300 mg of test formulations is less than that of 1000 mg reference preparation.

Example 2

| | Formulation 5 | |
|---|---|---|
| | mg/tablet | ratio (%) |
| Abiraterone Acetate | 150.000 | 23.56 |
| Hydroxy propyl methylcellulose E5 LV | 38.462 | 6.04 |
| Sodium dodecyl sulfate | 3.846 | 0.60 |
| sodium 8 - (salicylamido) caprylate | 150.000 | 23.56 |
| lactose | 240.000 | 37.69 |
| Crosslinked povidone XL | 48.000 | 7.54 |
| Magnesium stearate | 6.495 | 1.02 |
| Total weight | 636.803 | 100.01 |

1) Preparation of Nanosuspension

Hydroxypropyl methylcellulose LV (0.212 kg) and sodium dodecyl sulfate (0.021 kg) were added into purified water (8.1 kg) and dissolved in it. Abiterone acetate (0.825 kg) was then added and stirred to dispersion. Two batches of above suspension were prepared for use.

The above three batches of dispersed suspension were added into the formulation tank of MULTI LAB grinding machine (0.3 mm zirconia grinding beads) and grinded under stirring to obtain the nano suspension of abiraterone acetate which has D90 of 455 nm, D50 of 227 nm, D10 of 99.3 nm, average particle size of 211.3 nm, and particle size distribution index PDI of 0.169.

2) Granulation 2.250 kg of sodium 8-(salicylamido) caprylate was added into the above nanosuspention and stirred, which was then added into the prescription amount of lactose and crosslinked povidone XL for MP3 Advanced fluidized bed granulation. After granulation, the granules are dried and pelleted.

3) Tabletting

The granules obtained above were mixed with magnesium stearate, and then pressed according to the theoretical tablet weight of 636.803 mg in the range of 95.0%-105.0%.

In Vitro Dissolution Test

According to the second method (paddle method) for dissolution determination in Chinese Pharmacopoeia (2015 Edition), 900 ml phosphate solution containing 0.25% SDS at pH 6.8 was used as dissolution medium for dissolution test. The specific dissolution rate data were shown in table 7 below. The dissolution test was carried out according to the second method of dissolution determination (paddle method) in Chinese Pharmacopoeia (2015 Edition) with 900 ml of phosphate buffer solution with pH 6.8 containing 0.25% SDS as the dissolution medium. The specific dissolution rate are shown in table 7 below.

TABLE 7

| | Dissolution rate Formulation 5 | | | |
|---|---|---|---|---|
| Time (min) | API | RSD | SNAC | RSD |
| 5 min | 9 | 8.1 | 10 | 5.9 |
| 10 min | 20 | 6.6 | 22 | 5.5 |
| 15 min | 32 | 5.7 | 33 | 5.1 |
| 20 min | 43 | 5.5 | 44 | 5.2 |

TABLE 7-continued

| | Dissolution rate Formulation 5 | | | |
|---|---|---|---|---|
| Time (min) | API | RSD | SNAC | RSD |
| 25 min | 52 | 4.9 | 53 | 4.8 |
| 30 min | 61 | 4.5 | 62 | 4.3 |
| 45 min | 81 | 3.6 | 81 | 3.4 |
| 60 min | 93 | 2.5 | 94 | 2.4 |

Test Example 2

In Vivo Pharmacokinetics Study in Healthy Subjects 2.1 Study Objectives

To study the pharmacokinetic characteristics of 75 mg, 150 mg, 300 mg and 450 mg doses of abiraterone acetate tablets in healthy subjects after a single oral administration under fasting state.

2.2 Study Plan

A single-center, open-label, sequential trial design was applied. A total of 16 healthy male subjects were planned to be enrolled in the study, who entered the four dose groups sequentially and the washout period of each dose group was seven days. Blood samples were collected at a series of time points, and safety test was performed. The blood concentration of abiraterone at different time points after dosing was determined by HPLC-MS/MS. Pharmacokinetic parameters were calculated using non-compartmental model and statistically analyzed.

2.3 Dosing Regimen

The subjects were admitted to the ward before dinner on the day before the administration of each studied dose. They had a standardized light diet in the evening, and then were fasting for solids and liquids overnight. They were fasting for at least 10 hours before dosing. According to the trial protocol, subjects were given a single oral administration of the investigational drug, abiraterone acetate tablets, 75 mg (split 150 mg tablet along the score line into half a tablet), 150 mg (150 mg×1 tablet), 300 mg (150 mg×2 tablets) and 450 mg (150 mg×3 tablets) with 240 mL water under fasting state in the morning on the day of trial of each dose group. Liquid was prohibited before administration and within 1 h after administration, and standard lunch and dinner (a standardized light diet) were taken about 4 and 10 h after administration.

2.4 Investigational Drug

Test Formulation (T): Abiraterone acetate tablets (Formulation 5), specification: 150 mg.

2.5 Pharmacokinetic Results

PKPS (PKPS, all enrolled in the group and receiving the study drug, at least one subject with analyzable PK parameters during the trial) was used for the statistical analysis of pharmacokinetic parameters.

In this study, 16 healthy subjects were enrolled, and a total of 16 subjects were included in the PKPS. One subject was withdrawn from this trial before dosing in group B due to increased uric acid.

The main pharmacokinetic parameters of abiraterone and SNAC of four dose groups A/B/C/D after single oral administration of abiraterone acetate tablet are shown in Tables 8 and 9 below.

TABLE 8

Main Pharmacokinetic Parameters of Abiraterone of Different Dose Groups after A Single Oral administration Mean ± SD (% CV)

| PK Parameters (Unit) | Dose group A 75 mg (N = 16) | Dose group B 150 mg (N = 15) | Dose group C 300 mg (N = 15) | Dose group D 450 mg (N = 15) |
|---|---|---|---|---|
| $C_{max}$ (ng/mL) | 33.9 ± 12.9 (38.1) | 81.4 ± 45.0 (55.3) | 209 ± 142 (67.8) | 405 ± 428 (106) |
| $AUC_{0-t}$ (ng·h/mL) | 98.96 ± 46.29 (46.77) | 246.11 ± 97.19 (39.49) | 620.08 ± 370.19 (59.70) | 1041.37 ± 903.24 (86.74) |
| $AUC_{0-\infty}$ (ng·h/mL) | 101.27 ± 46.61 (46.02) | 250.27 ± 97.95 (39.14) | 627.60 ± 370.44 (59.02) | 1054.58 ± 904.86 (85.80) |
| $T_{max}$ * (h) | 1.13 (0.5-2.5) | 1.0 (0.5-1.25) | 1.0 (0.5-2.00) | 1.0 (0.75-3.00) |
| $t_{1/2z}$ (h) | 10.15 ± 3.1 (30.52) | 10.71 ± 2.03 (18.96) | 10.62 ± 1.80 (16.94) | 10.85 ± 1.51 (13.95) |
| $\lambda_z$ (h$^{-1}$) | 0.08 ± 0.04 (45.65) | 0.07 ± 0.02 (24.09) | 0.07 ± 0.01 (17.06) | 0.07 ± 0.01 (14.69) |
| $AUC_{\%\ Extrap}$ (%) | 2.74 ± 1.52 (55.45) | 1.77 ± 0.85 (48.03) | 1.39 ± 0.72 (51.56) | 1.60 ± 0.76 (47.31) |
| $V_z/F$ (×10$^3$ L) | 12.31 ± 5.1 (41.23) | 10.7 ± 4.7 (43.86) | 9.1 ± 4.1 (45.59) | 9.2 ± 3.95 (43.17) |
| $CL_z/F$ (×10$^2$ L·h$^{-1}$) | 9.26 ± 4.67 (50.44) | 6.82 ± 2.41 (35.52) | 5.79 ± 2.2 (38.69) | 5.79 ± 2.43 (42.04) |
| $MRT_{0-t}$ (h) | 5.36 ± 1.64 (30.49) | 5.79 ± 1.06 (18.26) | 5.7 ± 0.96 (16.83) | 5.68 ± 1.34 (23.58) |
| $MRT_{0-\infty}$ (h) | 6.56 ± 1.88 (28.73) | 6.82 ± 1.47 (21.49) | 6.51 ± 1.34 (20.6) | 6.6 ± 1.72 (26.01) |

* $T_{max}$ is expressed using median (minimum-maximum).

TABLE 9

Main Pharmacokinetic Parameters of SNAC of Different Dose Groups after A Single Oral administration Mean ± SD (% CV)

| PK Parameters (Unit) | Dose group A 75 mg (N = 16) | Dose group B 150 mg (N = 15) | Dose group C 300 mg (N = 15) | Dose group D 450 mg (N = 15) |
|---|---|---|---|---|
| $C_{max}$ (ng/mL) | 407 ± 140 (34.4) | 977 ± 385 (39.4) | 1870 ± 484 (25.9) | 2460 ± 963 (39.2) |
| $AUC_{0-t}$ (ng · h/mL) | 291.34 ± 61.44 (21.09) | 668.36 ± 153.26 (22.93) | 1396.58 ± 284.15 (20.35) | 2121.8 ± 491.85 (23.18) |
| $AUC_{0-\infty}$ (ng · h/mL) | 294.82 ± 61.4 (20.83) | 672.15 ± 152.2 (22.64) | 1409.79 ± 285.05 (20.22) | 2131.49 ± 490.78 (23.03) |
| $T_{max}$ * (h) | 0.38 (0.25-1.25) | 0.5 (0.25-0.75) | 0.5 (0.25-1.75) | 0.5 (0.25-0.75) |
| $t_{1/2z}$ (h) | 3.53 ± 2.54 (71.79) | 2.94 ± 1.39 (47.26) | 5.35 ± 3.92 (73.26) | 4.88 ± 2.37 (48.47) |
| $\lambda_z$ (h$^{-1}$) | 0.28 ± 0.14 (49.45) | 0.29 ± 0.14 (46.65) | 0.19 ± 0.11 (58.63) | 0.18 ± 0.09 (48.95) |
| $AUC_{\_\%\ Extrap}$ (%) | 1.23 ± 1.12 (91.06) | 0.63 ± 0.62 (97.47) | 0.95 ± 0.91 (95.91) | 0.50 ± 0.44 (87.05) |
| $V_z/F$ (×10$^3$ L) | 1.28 ± 0.88 (68.58) | 1.01 ± t0.63 (62.71) | 1.74 ± 1.28 (73.48) | 1.52 ± 0.66 (43.62) |
| $CL_z/F$ (×10$^2$ L · h$^{-1}$) | 2.66 ± 0.64 (23.96) | 2.36 ± 0.62 (26.11) | 2.22 ± 0.51 (23.04) | 2.22 ± 0.51 (23.3) |
| $MRT_{0-t}$(h) | 1.32 ± 0.52 (39.31) | 1.21 ± 0.48 (39.74) | 1.28 ± 0.36 (28.37) | 1.40 ± 0.53 (37.74) |
| $MRT_{0-\infty}$(h) | 1.58 ± 0.76 (48.31) | 1.32 ± 0.5 (38.27) | 1.55 ± 0.54 (35.01) | 1.53 ± 0.51 (33.51) |

* $T_{max}$ is expressed using median (minimum-maximum)

2.6 Analysis of Statistical Results

1) Dose Linearity Analysis

The linearity between AUC and $C_{max}$ and the administration dose was analyzed by confidence interval method, and linear regression analysis was performed on the AUC and $C_{max}$ after natural logarithmic transformation respectively and the administration dose, to observe the slope of the linear regression equation and 90% confidence interval. The analysis results are shown in Table 10 below.

The results show that: within the dose range of 75-450 mg of test Formulation(T), the β values of $C_{max}$, $AUC_{0-t}$ and $AUC_{0-\infty}$ of abiraterone are 1.27, 1.29, and 1.29, respectively, which are all within the range of 0.5-2.0, indicating that test Formulation(T) has the tendency of linear dynamic characteristics within the dose range of 75-450 mg. Moreover, the 90% confidence intervals of the β values of $C_{max}$, $AUC_{0-t}$ and $AUC_{0-\infty}$ of abiraterone are 1.15-1.38, 1.22-1.37, and 1.21-1.36, respectively, which basically fall within the judgment range of 0.61-1.39, indicating that test Formulation(T) has linear dynamic characteristics.

Within the dose range of 75-450 mg of test Formulation (T) (the content of SNAC was equivalent to that of the main active pharmaceutical ingredient), the β values of $C_{max}$, $AUC_{0-t}$ and $AUC_{0-\infty}$ of SNAC are 1.00, 1.10, and 1.10, respectively, which are all within the range of 0.8-1.25, indicating that SNAC has the tendency of linear dynamic characteristics within the dose range of 75-450 mg. Moreover, the 90% confidence intervals of the β values of $C_{max}$, $AUC_{0-t}$ and $AUC_{0-\infty}$ of SNAC are 0.90-1.10, 1.07-1.14, and 1.06-1.14, respectively, which basically fall within the judgment range of 0.88-1.12, indicating that the SNAC has linear dynamic characteristics.

TABLE 10

Results of Linear Pharmacokinetic Characteristics of Pharmacokinetic Parameters by the Confidence Interval Method (N = 16)

| Analyte | PK parameter | Slope of the linear regression equation (β) | 90% confidence interval of β | Judgment range |
|---|---|---|---|---|
| Abiraterone | $LnC_{max}$ | 1.27 | 1.15-1.38 | 0.61-1.39 |
| | $LnAUC_{0-t}$ | 1.29 | 1.22-1.37 | 0.61-1.39 |
| | $LnAUC_{0-\infty}$ | 1.29 | 1.21-1.36 | 0.61-1.39 |
| SNAC | $LnC_{max}$ | 1.00 | 0.90-1.10 | 0.88-1.12 |
| | $LnAUC_{0-t}$ | 1.10 | 1.07-1.14 | 0.88-1.12 |
| | $LnAUC_{0-\infty}$ | 1.10 | 1.06-1.14 | 0.88-1.12 |

Note:
As abiraterone acetate is a highly variable drug under fasting conditions, the judgment range can be relaxed to 0.5-2.0 according to the literatrue "Hummel J, McKendrick S, Brindley C, et al. Exploratory assessment of dose proportionality: review of current approaches and proposal for a practical criterion. Pharm Stat, 2009, 8: 38-49.

2) Pharmacokinetic Conclusion

After oral administration of test Formulation(T), the mean peak concentration ($C_{max}$) of abiraterone in groups A-D is 33.9, 81.4, 209 and 405 ng/mL, respectively. The mean exposure ($AUC_{0-t}$) is 98.96, 246.11, 620.08 and 1,041.37 ng·h/mL, respectively. The median time to peak plasma concentration ($T_{max}$) is 1.13 h, 1.0 h, 1.0 h and 1.0 h, respectively. The mean volume of distribution (Vz/F) is 12.31, 10.7, 9.1 and 9.2×10$^3$ L, respectively. The mean elimination half-life ($t_{1/2}$) is 10.15, 10.71, 10.62 and 10.85 h, respectively. The mean plasma clearance (CLz/F) is 9.26, 6.82, 5.79 and 5.79×10$^2$ L/h, respectively. There are basically no statistically significant differences among the various dose groups for the drug distribution and elimination related parameters, Vz, t½z and $C_{Lz}$. Compared with the previously reported data (analysis results are shown in Table 11), the exposure ($C_{max}$ and AUC) of 300 mg test Formulation(T) is in line with expectations, i.e. the exposure dose is not lower than that of 1,000 mg branded drug.

TABLE 11

Main Pharmacokinetic Parameters of Oral Administration of Two Types of Abiraterone Acetate Tablets

| PK Parameter (Unit) | Abiraterone acetate tablets (Zytiga ®) [1] | Test Formulation (T) |
|---|---|---|
| Dose (mg) | 1000 | 300 |
| N | 433 (POOLED) | 16 |
| $T_{max}$ * (h) | 2 (1-8) | 1 (0.5-2) |
| $C_{max}$ (ng/mL) | 93.5 (58.6) | 209.5 (142.1) |
| $AUC_{0-c}$ (ng · h/mL) | 503 (299) | 627.6 (370.4) |
| $t_{1/2z}$ (h) | 15.2 (4.0) | 10.6 (1.80) |

Note:
[1] Excerpt from FDA.ZYTIGA ®, CENTER FOR DRUG EVALUATION AND RESEARCH, APPLICATION NUMBER: 202379Orig1s000, PHARMACOLOGY REVIEW(S)

After oral administration of test Formulation (T), the mean peak concentration ($C_{max}$) of SNAC in groups A-D is 407, 977, 1,870 and 2,460 ng/mL, respectively. The mean exposure ($AUC_{0-t}$) is 291.34, 668.36, 1,396.58 and 2,121.8 ng·h/mL, respectively. The median time to peak plasma concentration ($T_{max}$) is 0.38 h, 0.5 h, 0.5 h and 0.5 h, respectively. The mean volume of distribution ($V_z/F$) is 1.28, 1.01, 1.74 and 1.52×10³ L, respectively. The mean elimination half-life ($t_{1/2}$) is 3.53, 2.94, 5.35 and 4.88 h, respectively. The mean plasma clearance ($CL_z/F$) is 2.66, 2.36, 2.22 and 2.22×10² L/h, respectively. There are no statistical differences among the various dose groups for the drug distribution and elimination related parameters, $V_z$, $t_{1/2z}$ and $CL_z$.

Test Example 3

In Vivo Food Effects Study in Healthy Subjects 3.1 Study Objectives

To study the effect of food on the pharmacokinetic characteristics of abiraterone acetate tablets through a single oral administration of abiraterone acetate tablets under fasting state or after meal, or a single oral administration of abiraterone acetate tablets (Zytiga®) produced by Patheon Inc. under modified fasting state, in healthy subjects.

3.2 Study Plan

A single-center, randomized, open-label, three-period, self-controlled crossover trial design was applied. A total of 24 healthy male subjects were planned to be enrolled in the study. The washout period between each dose group was seven days. Blood samples were collected at a series of time points, and safety test was performed. The HPLC-MS/MS method was used to determine the plasma concentration of abiraterone and SNAC at different time points after drug administration. The non-compartmental model was used to calculate the pharmacokinetic parameters, and statistical analysis was performed.

3.3 Dosing Regimen

The subjects were orally administered a single dose of the test formulation (T) under fasting state at a dose of 300 mg (150 mg×2 tablets), a single dose of the test formulation (T) of 300 mg abiraterone acetate tablets (I) (150 mg×2 tablets) after a high-fat meal (the total calories were approximately 800~1,000 kcal, wherein approximately 50% of the calories were derived from fat; the test meal of each test cycle for the postprandial administration should be consistent; a high-fat meal was given 30 minutes before drug administration and should be finished within 30 minutes), or a single dose of the reference preparation of 1,000 mg abiraterone acetate tablets (Zytiga®) (250 mg×4 tablets) under modified fasting state (a medium-fat meal was given two hours before drug administration and one hour after drug administration; the total calories were approximately 450 kcal wherein 30% of the calories were derived from fat; the meal should be finished within 30 minutes), with 240 mL of warm water, in the morning on the day of drug administration for each cycle. Liquid was prohibited before administration and one hour after drug administration, and a standard lunch and dinner (a standardized light diet) were given approximately 4 and 10 hours after drug administration. The drug was swallowed whole instead of being sucked or chewed.

3.4 Investigational Drug

Test Formulation (T): Abiraterone acetate tablets (Formulation 5), specification: 150 mg;

Reference Preparation (R): Abiraterone Acetate Tablets; produced by Patheon Inc.; trade name: Zytiga®; specification: 250 mg.

3.5 Pharmacokinetic Results

The PKPS was used for the statistical analysis of pharmacokinetic parameters.

Twenty-four healthy subjects were enrolled in this study, and a total of 24 subjects were included in the PKPS. One subject was withdrawn from this trial after completing Cycle 1 due to increased blood bilirubin. The main PK parameters of abiraterone in each dose groups after single oral administration of abiraterone acetate tablet under fasting state are shown in Table 12 and 13 below.

TABLE 12

Main Pharmacokinetic Parameters After Oral Administration of abiraterone acetate tablets (Fasting), abiraterone acetate tablets (After a High-Fat Meal), and Reference Preparation (R) (Modified Fasting), Mean ± SD (% CV)

| Pharmacokinetic Parameters (Unit) | Grouping Information (Mean ± SD) | | |
|---|---|---|---|
| | Test Formulation Under Fasting State (N = 23) | Test Formulation After a High-Fat Meal (N = 24) | Reference Preparation Under Modified Fasting State (N = 23#) |
| $C_{max}$ (ng/mL) | 177 ± 102 (57.7) | 393 ± 193 (49.2) | 2160 ± 858 (39.8) |
| $AUC_{0-t}$ (ng · h/mL) | 513.45 ± 207.46 (40.40) | 992.75 ± 325.77 (32.81) | 4226.25 ± 1269.37 (30.04) |
| $AUC_{0-\infty}$ (ng · h/mL) | 521.63 ± 208.06 (39.89) | 1007.84 ± 335.75 (33.31) | 4271.93 ± 1292.73 (30.26) |
| $T_{max}$ * (h) | 1.00 (0.50, 5.00) | 1.50 (1.00, 5.00) | 1.50 (1.25, 3.00) |
| $t_{1/2}$ (h) | 9.78 ± 2.8 (28.63) | 10.83 ± 2.82 (26.06) | 9.93 ± 2.54 (25.62) |
| $V_z/F$ (mL) | 9404.17 ± 4619.55 (49.12) | 4980.33 ± 1531.55 (30.75) | 3735.25 ± 1844.13 (49.37) |

TABLE 12-continued

Main Pharmacokinetic Parameters After Oral Administration of abiraterone acetate tablets (Fasting), abiraterone acetate tablets (After a High-Fat Meal), and Reference Preparation (R) (Modified Fasting), Mean ± SD (% CV)

| Pharmacokinetic Parameters (Unit) | Test Formulation Under Fasting State (N = 23) | Test Formulation After a High-Fat Meal (N = 24) | Reference Preparation Under Modified Fasting State (N = 23#) |
|---|---|---|---|
| $CL_z/F$ (mL · h$^{-1}$) | 664.24 ± 256.15 (38.56) | 335.86 ± 130.6 (38.89) | 262.45 ± 103.28 (39.35) |
| $\lambda_z$ (h$^{-1}$) | 0.08 ± 0.02 (29.19) | 0.07 ± 0.02 (33.02) | 0.07 ± 0.02 (24.20) |
| $MRT_{0-t}$ (h) | 6.13 ± 2.16 (35.27) | 5.64 ± 1.56 (27.60) | 4.93 ± 1.24 (25.23) |
| $MRT_{0-\infty}$ (h) | 7.09 ± 3.06 (43.11) | 6.43 ± 2.04 (31.78) | 5.53 ± 1.79 (32.48) |
| $AUC_{\_\% Extrap}$ (%) | 1.69 ± 1.68 (99.42) | 1.34 ± 1.06 (78.72) | 1.02 ± 1.01 (99.39) |

* $T_{max}$ is expressed by median (minimum-maximum).

TABLE 13

Main Pharmacokinetic Parameters of SNAC After a Single Oral Administration of abiraterone acetate tablets (Fasting), abiraterone acetate tablets (After a High-Fat Meal), Mean ± SD (% CV)

| Pharmacokinetic Parameters (Unit) | Test Formulation Under Fasting State (N = 23) | Test Formulation After a High-Fat Meal (N = 24) |
|---|---|---|
| $C_{max}$ (ng/mL) | 1580 ± 697 (44.1) | 1120 ± 574 (51.4) |
| $AUC_{0-t}$ (ng · h/mL) | 1246.29 ± 304.53 (24.43) | 1541.7 ± 246.83 (16.01) |
| $AUC_{0-\infty}$ (ng · h/mL) | 1254.58 ± 306.16 (24.4) | 1548.48 ± 245.02 (15.82) |
| $T_{max}$ * (h) | 0.50 (0.25, 5.00) | 1.13 (0.50, 5.00) |
| $t_{1/2}$ (h) | 4.22 ± 1.71 (40.60) | 3.06 ± 1.19 (38.98) |
| $V_z/F$ (mL) | 1617.33 ± 948.82 (58.67) | 869.66 ± 362.41 (41.67) |
| $CL_z/F$ (mL · h$^{-1}$) | 255.02 ± 72.16 (28.3) | 198.03 ± 28.78 (14.53) |
| $\lambda_z$ (h$^{-1}$) | 0.19 ± 0.08 (42.75) | 0.27 ± 0.12 (45.94) |
| $MRT_{0-t}$ (h) | 1.59 ± 1.35 (84.59) | 2.28 ± 0.99 (43.45) |
| $MRT_{0-\infty}$ (h) | 1.74 ± 1.38 (79.42) | 2.36 ± 1 (42.2) |
| $AUC_{\_\% Extrap}$ (%) | 0.66 ± 0.54 (81.44) | 0.46 ± 0.63 (134.49) |

With the dosing order, dosing cycle and dosing regimen as fixed effects, the subjects were included as random effects in the linear mixed model as random effects. The least-squares mean ratio of $C_{max}$, $AUC_{0-t}$ and $AUC_{0-\infty}$ of abiraterone in plasma after oral administration of the test formulation T under a high-fat meal or fasting states, and its 90% confidence interval were calculated. The analysis results are shown in Table 14.

According to literature reports (See Table 15), the $C_{max}$ and $AUC_{0-t}$ of abiraterone after oral administration of 1,000 mg ZYTIGA® under high-fat meal conditions are approximately 16.8 times and 9.92 times of that in a fasting state, respectively, and the $C_{max}$ and $AUC_{0-t}$ of abiraterone after oral administration of 1,000 mg ZYTIGA® under modified fasting state are 11.7 times and 7.49 times of that in a fasting state, respectively. The $C_{max}$ and $AUC_{0-t}$ of abiraterone after oral administration of 500 mg YONSA® after a high-fat meal are 6.50 times and 4.59 times of that in a fasting state, respectively.

The test results show that: after oral administration of the test formulation, abiraterone acetate tablets after a high-fat meal, the $C_{max}$ of abiraterone is approximately 2.19 times of that in the fasting state, $AUC_{0-t}$ is approximately 1.97 times of that in the fasting state, and $AUC_{0-\infty}$ is approximately 1.96 times of that in the fasting state. Abiraterone acetate tablet has certain food effect. However, comparing with the food effects of ZYTIGA® and YONSA® as reported in the literature, the effect of food on the modified formulation of abiraterone acetate tablet is significantly lower.

Abiraterone acetate tablet, ZYTIGA®, developed by Johnson & Johnson, is largely affected by food. Furthermore, considering the diversity and variability of food, taking them with food may lead to increased exposure and abnormal changes. Therefore, the package insert of ZYTIGA® clearly requires patients to abstain from food two hours before drug administration and one hour after drug administration. Based on the present test results, abiraterone acetate tablet (T) shows a relatively low food effect, so the use of abiraterone acetate tablet (T) without eating restrictions can be considered in the later stage, improving compliance of patient and convenience of drug administration.

TABLE 14

Ratio of AUC to $C_{max}$ of Abiraterone in Subjects After Oral Administration of the Test Formulation T Under High-Fat Meal/Fasting State and Its 90% Confidence Interval

| Parameters | Geometric Mean and Ratio | | | |
|---|---|---|---|---|
| | T After a High-Fat Meal (N = 24) | T Under Fasting State After a High-Fat Meal (N = 23) | (T After a High-Fat Meal/T Under Fasting Satate) % | 90% Confidence Interval |
| $C_{max}$ (ng/mL) | 339.77 | 155.49 | 218.52 | 170.02%~280.85% |
| $AUC_{0-t}$ (ng · h/mL) | 938.97 | 477.76 | 196.53 | 168.60%~229.10% |
| $AUC_{0-\infty}$ (ng · h/mL) | 951.78 | 486.15 | 195.78 | 168.12%~227.99% |

TABLE 15

Relative Bioavailability of Abiraterone After Oral Administration of ZYTIGA ® and YONSA ® in Different Dietary States

| Parameter GMR (Fed/Fasted %) | ZYTIGA ® 1000 mg (After a High-Fat Meal/Fasting) % | ZYTIGA ® 1000 mg (Modified Fasting/Fasting) % | YONSA ® 500 mg (After a High-Fat Meal/Fasting) % |
|---|---|---|---|
| $C_{max}$ (ng/mL) | 1683 | 1169.5 | 649.5 |
| $AUC_{0-t}$ (hr* ng/mL) | 992 | 773.6 | 458.6 |
| $AUC_{0-\infty}$ (hr* ng/mL) | 969 | 749.2 | 442.4 |

Note:
* $C_{max}$, N = 41; $AUC_{0-t}$, N = 41; $AUC_{0-\infty}$, N = 37; [1] Excerpt from FDA.ZYTIGA ®, CENTER FOR DRUG EVALUATION AND RESEARCH, APPLICATION NUMBER: 202379Orig1s000, PHARMACOLOGY REVIEW(S); [2] Excerpt from FDA.YONSA ®, CENTER FOR DRUG EVALUATION AND RESEARCH, APPLICATION NUMBER: 210308Orig1s000, PHARMACOLOGY REVIEW(S) and [J]. Cancer chemotherapy and pharmacology, 2015, 75(1): 49-58.

With the dosing orders, dosing cycle and dosing regimen as fixed effects, the subjects were included as random effects in the linear mixed model. The least-squares mean ratio of $C_{max}$, $AUC_{0-t}$ and $AUC_{0-\infty}$ of abiraterone in plasma after oral administration of the test formulation T under a high-fat meal and oral administration of the reference formulation R under modified fasting states, and its 90% confidence interval were calculated. The analysis results are shown in Table 16.

The results show that: the $C_{max}$, $AUC_{0-t}$ and $AUC_{0-\infty}$ of the test formulation (T) under the effect of a high-fat meal are 339.77 ng/mL, 938.97 ng·h/mL and 951.78 ng·h/mL, respectively. The $C_{max}$, $AUC_{0-t}$ and $AUC_{0-\infty}$ of the reference formulation under modified fasting states are 2,000.25 ng/mL, 4,037.82 ng·h/mL and 4,079.87 ng·h/mL, respectively. The exposure of 300 mg the test formulation T orally administered under high-fat meal is far lower than that of the reference formulation, 1,000 mg ZYTIGA®, under modified fasting conditions. Comparing with the exposure to the reference formulation under modified fasting conditions, the $C_{max}$ of the test formulation, orally administered after a high-fat meal is approximately 16.99%, $AUC_{0-t}$ is approximately 23.25%, and $AUC_{0-\infty}$ is approximately 23.33%. This shows that the maximum exposure to the test formulation T under the effect of a high-fat meal is under the upper limit of exposure of ZYTIGA® under the package insert conditions.

TABLE 16

Ratio of AUC to $C_{max}$ of Abiraterone in Subjects After Oral Administration of Test Formulation T After a High-Fat Meal and Oral Administration of Reference Formulation R Under Modified Fasting States and Its 90% Confidence Interval

| Parameter | Geometric Mean and Ratio | | | |
|---|---|---|---|---|
| | T After a High-Fat Meal (N = 24) | R Under Modified Fasting States (N = 23) | (T Under High-Fat Meal Conditions/ R Under Modified Fasting States) % | 90% Confidence Interval |
| $C_{max}$ (ng/mL) | 339.77 | 2000.25 | 16.99 | 13.22%~21.83% |
| $AUC_{0-t}$ (ng · h/mL) | 938.97 | 4037.82 | 23.25 | 19.95%~27.11% |
| $AUC_{0-\infty}$ (ng · h/mL) | 951.78 | 4079.87 | 23.33 | 20.03%~27.17% |

Test Example 4

The Comparative PK Study of Abiraterone Acetate Tablets in Human after Single Dose 4.1 Study Objectives To study the pharmacokinetic characteristics of abiraterone acetate tablets after oral administration of a single dose in healthy subjects under fasting state, using the marketed abiraterone acetate tablets (Zytiga®) as reference preparation. The main pharmacokinetic parameters of the two formulations are compared and the relative bioavailability of the two formulations are evaluated. The effect of SNAC in the test formulations on pharmacokinetics of the combined prednisone and active metabolite prednisolone is observed.

4.2 Study Plan

A single-center, randomized, open-label, 4-cycle repeation, crossover trial design was applied. The bioavailability under fasting state is studied. A total of 36 healthy male subjects were planned to be enrolled in the study. The washout period between cycles was 7 days. Blood samples were collected at a serial of time points, and safety test was performed. HPLC-MS/MS was used to measure blood concentration of abiraterone, SNAC, prednisone, and prednisolone at different time points after administration of the drug. Pharmacokinetic parameters were calculated using non-compartmental model and statistically analyzed.

4.3 Dosing Regimen

The subjects were admitted to ward before dinner on the day before the administration in each cycle. They had a standardized light diet in the evening, and then were fasting for solids and liquids overnight. They were fasting for at least 10 hours before dosing. The subjects were given a single oral administration of 300 mg of the test abiraterone acetate tablets (I) (150 mg×2 tablets) and 5 mg of prednisone tablets, or 1000 mg of the reference preparation of abiraterone acetate tablets (Zytiga®) (250 mg×4 tablets) and 5 mg of prednisone tablets with 240 mL of water under fasting state in the morning on the day of the trial. Liquid was prohibited before administration and within 1 h after administration, and standard lunch and dinner (a standardized light diet) were taken about 4 and 10 h after administration.

4.4 Investigational Drug

Test Formulation (T): Abiraterone acetate tablets (Formulation 5), specification: 150 mg.

Reference Preparation (R): Abiraterone Acetate Tablets; produced by Patheon Inc.; trade name: Zytiga®; specification: 250 mg.

Concurrent drugs: Prednisone Acetate Tablets: Manufacturer: Shanghai Sine Pharmaceutical Laboratories Co., Ltd.

4.5 Result

1) Pharmacokinetic Parameters

Analysis of blood concentrations was conducted based on PKCS.

After a single oral administration of abiraterone acetate 300 mg+prednisone 5 mg or Zytiga® 1000 mg+prednisone 5 mg under fasting state, the main pharmacokinetic parameters of abiraterone are shown in Table 17, and the main pharmacokinetic parameters of prednisone and active metabolite prednisolone are shown in Table 18 and Table 19.

TABLE 17

The main pharmacokinetic parameters of abiraterone after a single oral administration of abiraterone acetate tablets 300 mg/Zytiga ® 1000 mg + prednisone tablets 5 mg in healthy subjects Mean ± SD (% CV)

| | Arithmetic Mean ± SD (% CV) | |
| --- | --- | --- |
| Parameter (Units) | Test Preparations (N = 36) | Reference Preparations (N = 35) |
| $T_{max}$* (h) | 1.25 (0.75, 4.50) | 1.50 (0.75, 4.50) |
| $C_{max}$ (ng/mL) | 171 ± 84.3 (49.4) | 161 ± 76.5 (47.4) |
| $AUC_{0-t}$ (ng · h/mL) | 500.09 ± 209.34 (41.86) | 560.86 ± 307.79 (54.88) |
| $AUC_{0-\infty}$ (ng · h/mL) | 509.00 ± 214.35 (42.11) | 579.58 ± 315.43 (54.42) |
| $\lambda z$ ($h^{-1}$) | 0.07 ± 0.02 (33.54) | 0.06 ± 0.03 (39.55) |
| $t_{1/2}$ (h) | 10.30 ± 2.80 (27.23) | 12.45 ± 5.24 (42.09) |
| $V_z/F$ (L) | 10237.30 ± 5111.45 (49.93) | 39711.20 ± 25733.45 (64.80) |
| $CL_z/F$ (L · $h^{-1}$) | 719.67 ± 390.55 (54.27) | 2386.19 ± 1971.83 (82.64) |
| $MRT_{0-t}$ (h) | 6.06 ± 1.52 (25.05) | 7.35 ± 1.53 (20.88) |
| $MRT_{0-\infty}$ (h) | 7.05 ± 2.23 (31.60) | 9.52 ± 3.77 (39.64) |

* Median (min-max) for $T_{max}$.

TABLE 18

The main pharmacokinetic parameters of prednisone after a single oral administration of abiraterone acetate tablets 300 mg/Zytiga ® 1000 mg + prednisone tablets 5 mg in healthy subjects Mean ± SD (% CV)

| | Arithmetic Mean ± SD (% CV) | |
| --- | --- | --- |
| Parameter (Units) | Test Preparatopms (N = 36) | Reference Preparations (N = 35) |
| $T_{max}$* (h) | 2.50 (1.25, 5.00) | 2.50 (1.50, 4.00) |
| $C_{max}$ (ng/mL) | 22.7 ± 2.82 (12.4) | 23.5 ± 3.39 (14.4) |
| $AUC_{0-t}$ (ng · h/mL) | 123.12 ± 16.72 (13.58) | 122.8 ± 17.75 (14.45) |
| $AUC_{0-\infty}$ (ng · h/mL) | 129.99 ± 18.54 (14.26) | 128.88 ± 19.53 (15.16) |
| $\lambda_z$ ($h^{-1}$) | 0.28 ± 0.03 (11.87) | 0.29 ± 0.03 (10.52) |
| $t_{1/2}$ (h) | 2.47 ± 0.30 (12.21) | 2.41 ± 0.24 (10.18) |
| $V_z/F$ (L) | 139 ± 19.96 (14.36) | 136.83 ± 19.02 (13.9) |
| $CL_z/F$ (L · $h^{-1}$) | 39.25 ± 5.72 (14.57) | 39.65 ± 5.81 (14.66) |
| $MRT_{0-t}$ (h) | 4.25 ± 0.36 (8.37) | 4.16 ± 0.36 (8.57) |
| $MRT_{0-\infty}$ (h) | 4.84 ± 0.55 (11.47) | 4.69 ± 0.49 (10.46) |

* Median (min-max) for $T_{max}$.

TABLE 19

The main pharmacokinetic parameters of prednisolone after a single oral administration of abiraterone acetate tablets 300 mg/Zytiga® 1000 mg + prednisone tablets 5 mg in healthy subjects Mean ± SD (% CV)

| | Arithmetic Mean ± SD (% CV) | |
|---|---|---|
| Parameter (Units) | TestPreparations (N = 36) | Reference Preparations (N = 35) |
| $T_{max}$ * (h) | 1.25 (0.50, 4.50) | 1.00 (0.50, 4.00) |
| $C_{max}$ (ng/mL) | 127 ± 20.8 (16.4) | 143 ± 21.1 (14.8) |
| $AUC_{0-t}$ (ng · h/mL) | 589.34 ± 95.47 (16.20) | 590.12 ± 96.88 (16.42) |
| $AUC_{0-\infty}$ (ng · h/mL) | 620.09 ± 105.59 (17.03) | 617.98 ± 105.89 (17.13) |
| $\lambda_z$ ($h^{-1}$) | 0.28 ± 0.02 (8.49) | 0.28 ± 0.02 (7.60) |
| $t_{1/2}$ (h) | 2.53 ± 0.22 (8.58) | 2.49 ± 0.19 (7.74) |
| $V_z/F$ (h) | 29.94 ± 3.79 (12.66) | 29.69 ± 4.37 (14.72) |
| $CL_z/F$ (L · $h^{-1}$) | 8.29 ± 1.38 (16.69) | 8.32 ± 1.41 (16.93) |
| $MRT_{0-t}$ (h) | 3.89 ± 0.38 (9.88) | 3.74 ± 0.37 (9.86) |
| $MRT_{0-\infty}$ (h) | 4.45 ± 0.50 (11.33) | 4.26 ± 0.45 (10.61) |

* Median (min-max) for $T_{max}$.

2) Relative Bioavailability of Abiraterone

The dosing order, preparations and cycles were considered as fixed effects. The preparation factors of different subjects were considered as random effects. The repeated measurements of preparations in individual subjects were also considered. The mixed-effect model was used to perform an analysis of variance for log-transformed values of $C_{max}$, $AUC_{0-t}$, and $AUC_{0-\infty}$, and ABE or RSABE method was used to evaluate relative bioavailability of abiraterone of the test preparations and the reference preparations. The relative bioavailability of abiraterone for the test preparation and the reference preparation is shown in Table 20. The results show that: after a single oral administration of the test abiraterone acetate tablets 300 mg+prednisone tablets 5 mg or the reference preparations Zytiga®1000 mg+prednisone tablets 5 mg in 36 healthy subjects under fasting state, $C_{max}$, $AUC_{0-t}$, and $AUC_{0-\infty}$ of abiraterone in the test preparation and the reference preparation are bioequivalent, i.e., under fasting atate, the exposure of the test preparation abiraterone acetate tablets 300 mg is equivalent to that of Zytiga® 1000 mg, providing preliminary support for efficacy of abiraterone acetate tablets 300 mg.

Comparing the intra-individual variations of abiraterone between the test preparation and the reference preparation, the intra-individual variations of $C_{max}$ are basically equivalent; however, the intra-individual variation of $AUC_{0-t}$ and $AUC_{0-\infty}$ of the test preparation are reduced by 10.58% and 11.34% respectively, compared with the reference preparation, and there were statistically significant of differences (p<0.01), suggesting that the exposure of abiraterone acetate tablets to human body is more stable than that of Zytiga®.

Non-parametric Kruskal-Wallis rank sum test was conducted for $T_{max}$ of abiraterone after oral administration of the test preparations and the reference preparations under fasting state, and there were statistically significant differences of $T_{max}$ of abiraterone (p<0.05), however the differences are not clinically significant, and would not influence safety and efficacy for clinical applications.

TABLE 20

Statistical results of relative bioavailability of abiraterone after oral administration of abiraterone acetate tablets 300 mg/Zytiga® 1000 mg + prednisone tablets 5 mg under fasting state (PKPS, N = 36)

| | Geometric mean and ratio | | | | Intra-individual | Intra-individual |
|---|---|---|---|---|---|---|
| Parameters | Test Preparations (T) (N = 36) | Reference Preparations (R) (N = 35) | GMR (%) | 90% Confidence interval | CVWR % of the reference preparations | CVWT % of the test preparations |
| $C_{max}$ (ng/mL) | 151.67 | 142.25 | 106.62 | 95.73~118.76 | 31.66 | 32.65 |
| $AUC_{0-t}$ (ng*h/mL) | 456.50 | 485.58 | 94.01 | 87.42~101.10 | 25.62 | 15.04 |
| $AUG_{0-\infty}$ (ng*h/mL) | 464.43 | 502.74 | 92.38 | 86.00~99.23 | 26.30 | 14.96 |

What is claimed is:

1. A pharmaceutical composition, comprising abiraterone acetate and an absorption enhancer, wherein the absorption enhancer is at least one selected from the group consisting of capric acid, sodium caprate, potassium caprate, N-(10-[2-hydroxybenzoyl]amino)capric acid, caprylic acid, sodium caprylate, potassium caprylate, N-(5-chlorosalicyloyl)-8-aminocaprylic acid, 8-(salicylamido)caprylic acid and sodium 8-(salicylamido)caprylate, wherein: a) the D90 value of abiraterone acetate is 400 to 600 nm, or b) the D50 value of abiraterone acetate is 150 to 300 nm.

2. The pharmaceutical composition according to claim 1, wherein a mean blood plasma $C_{max}$ of 209±142 ng/ml is provided upon orally administering 300 mg dose of abiraterone acetate to a group of healthy male subjects in a fasting state.

3. The pharmaceutical composition according to claim 1, wherein a median $T_{max}$ of 1 hour is provided upon orally administering 300 mg dose of abiraterone acetate to a group of healthy male subjects in a fasting state.

4. The pharmaceutical composition according to claim 1, wherein a mean blood plasma $AUC_{0-t}$ of 620.08±370.19 n·gh/ml is provided upon orally administering 300 mg dose of abiraterone acetate to a group of healthy male subjects in a fasting state.

5. The pharmaceutical composition according to claim 1, wherein a mean blood plasma $AUC_{0-\infty}$ of 627.60±370.44 n·gh/ml is provided upon orally administering 300 mg dose of abiraterone acetate to a group of healthy male subjects in a fasting state.

6. The pharmaceutical composition according to claim 1, further comprising lactose.

7. The pharmaceutical composition according to claim 6, wherein the lactose is present in an amount of 15 to 80%, relative to the total weight of the pharmaceutical composition.

8. The pharmaceutical composition according to claim 1, wherein the absorption enhancer is at least one of 8-(salicylamido)caprylic acid and sodium 8-(salicylamido)caprylate.

9. The pharmaceutical composition according to claim 1, wherein the weight ratio of the absorption enhancer to abiraterone acetate is 1:10 to 20:1.

10. The pharmaceutical composition according to claim 1, further comprising a disintegrant, wherein the disintegrant is at least one selected from the group consisting of croscarmellose sodium, crospovidone, sodium carboxymethyl starch, calcium carboxymethylcellulose, low-substituted hydroxypropyl cellulose, starch, pregelatinized starch and alginic acid.

11. The pharmaceutical composition according to claim 1, further comprising at least one stabilizer selected from the group consisting of cellulose derivatives and surfactants.

12. The pharmaceutical composition according to claim 1, wherein 80 to 125% of the mean blood plasma $AUC_{0-\infty}$ of 627.60 n·gh/mL is provided upon orally administering 300 mg dose of the abiraterone acetate pharmaceutical composition to a group of healthy male subjects in a fasting state.

13. The pharmaceutical composition according to claim 1, wherein 80 to 125% of the mean blood plasma $C_{max}$ of 209 ng/ml is provided upon orally administering 300 mg dose of the abiraterone acetate pharmaceutical composition to a group of healthy male subjects in a fasting state.

14. The pharmaceutical composition according to claim 1, wherein the mean blood plasma $C_{max}$ is up to 3 times that of the fasting state upon orally administering 300 mg dose of the abiraterone acetate pharmaceutical composition to a group of healthy male subjects in a high-fat statetimes.

15. The pharmaceutical composition according to claim 1, wherein the mean blood plasma $AUC_{0-t}$ is up to 3 times that of the fasting state upon orally administering 300 mg dose of the abiraterone acetate pharmaceutical composition to a group of healthy male subjects in a high-fat statetimes.

16. The pharmaceutical composition according to claim 1, comprising:
 a) 150 mg of abiraterone acetate,
 b) 10 to 40% by weight of an absorption enhancer,
 c) 0.5 to 20% by weight of a stabilizer,
 d) 25 to 75% by weight of lactose, and
 e) 0.5 to 20% by weight of a disintegrant,
 the pharmaceutical composition further comprises 0.1 to 2.0% by weight of a lubricant.

17. A method for preparing the pharmaceutical composition according to claim 1, comprising the steps of mixing abiraterone acetate with an absorption enhancer and optionally at least one excipient, and granulating through a fluidized bed, wherein the excipient is at least one selected from the group consisting of lactose and disintegrants.

18. A method for treating prostate cancer, comprising administering the pharmaceutical composition according to claim 1 at a daily dose of 300 mg.

19. The pharmaceutical composition according to claim 11, wherein the cellulose derivative is hydroxypropyl methyl cellulose, methyl cellulose, hydroxypropyl cellulose, hydroxyethyl cellulose or sodium carboxymethyl cellulose; the surfactant is polyoxyethylene ether, poloxamer, polyethylene glycol glyceride, polyoxyethylenated castor oil or polyethoxylated hydrogenated castor oil, sodium lauryl sulfate or sodium cholate.

20. The pharmaceutical composition according to claim 16, wherein the absorption enhancer is at least one of 8-(salicylamido)caprylic acid and sodium 8-(salicylamido)caprylate, and the stabilizer is at least one of hydroxypropyl methyl cellulose and sodium lauryl sulfate.

21. A pharmaceutical composition comprising a 300 mg dose of abiraterone acetate, an absorption enhancer and optionally at least one excipient, wherein the excipient is at least one selected from the group consisting of lactose and disintegrants.

* * * * *